United States Patent
Amini

(10) Patent No.: US 6,597,186 B2
(45) Date of Patent: Jul. 22, 2003

(54) THROUGH TANK LEVEL GAUGING

(75) Inventor: Bijan K. Amini, Houston, TX (US)

(73) Assignee: EM-Tech Sensors LLC, Houston, TX (US)

( * ) Notice: Subject to any disclaimer, the term of this patent is extended or adjusted under 35 U.S.C. 154(b) by 0 days.

(21) Appl. No.: 09/734,945

(22) Filed: Dec. 11, 2000

(65) Prior Publication Data
US 2002/0093343 A1 Jul. 18, 2002

Related U.S. Application Data

(60) Provisional application No. 60/170,281, filed on Dec. 10, 1999.

(51) Int. Cl.[7] .................. G01R 27/10; G01F 23/284
(52) U.S. Cl. .................. 324/644; 324/699; 73/290 R
(58) Field of Search ................... 324/644, 232, 324/228, 241, 334, 335, 340, 339, 699, 639, 640; 73/290 R; 340/618

(56) References Cited

U.S. PATENT DOCUMENTS

| | | |
|---|---|---|
| 3,574,458 A | 4/1971 | Hollis |
| 3,617,779 A | 11/1971 | Rosenberg |
| 3,851,236 A | 11/1974 | Dennhardt |
| 3,882,375 A * | 5/1975 | Zemanek, Jr. .............. 324/340 |
| 3,995,835 A | 12/1976 | Clichy |
| 4,679,936 A | 7/1987 | Gerharz |
| 5,038,107 A | 8/1991 | Gianzero |
| 5,132,623 A | 7/1992 | De |
| 5,150,446 A | 9/1992 | Penner |
| 5,260,661 A | 11/1993 | Vail |
| 5,283,520 A | 2/1994 | Martin |
| 5,426,367 A | 6/1995 | Martin |
| 5,610,517 A | 3/1997 | Ma |
| 5,633,182 A | 5/1997 | Miyawaki |
| 5,646,533 A * | 7/1997 | Locatelli et al. ............ 324/339 |
| 5,654,639 A * | 8/1997 | Locatelli et al. ............ 324/239 |
| 5,698,977 A | 12/1997 | Simpson |
| 5,751,144 A | 5/1998 | Weischedel |
| 5,942,894 A | 8/1999 | Wincheski |
| 5,969,254 A | 10/1999 | Yamaguchi |
| 6,008,657 A | 12/1999 | Suyama |
| 6,025,721 A | 2/2000 | Vail |
| 6,084,403 A | 7/2000 | Sinclair |
| 6,097,532 A | 8/2000 | Harris |
| 6,100,696 A | 8/2000 | Sinclair |
| 6,157,195 A | 12/2000 | Vail |
| 6,293,142 B1 * | 9/2001 | Pchelnikov et al. ......... 324/640 |

* cited by examiner

*Primary Examiner*—Christine Oda
*Assistant Examiner*—Anjan K. Deb
(74) *Attorney, Agent, or Firm*—David McEwing

(57) ABSTRACT

A method is provided for creating a spectral EM frequency to calculate the thickness of a material with unknown permeability and conductivity using metallic transparencies. The method comprises the steps of testing empirically to approximate the conductivity, testing empirically to approximate the permeability, creating a first set of electromagnetic waves adjacent to the material to be measured of a relatively low frequency, impinging the first set of electromagnetic waves on the material for saturating the material, creating a second set of electromagnetic waves having specific constant amplitude of a higher frequency than the first set of electromagnetic waves, the second set of electromagnetic waves for engaging the material and generating a sensing signal having modified characteristics, and receiving the sensing signal through the saturated material such that the modified characteristics of the sensing signal are processed to determine the thickness of the material.

10 Claims, 21 Drawing Sheets

THROUGH TANK LEVEL GAUGING

CROSS REFERENCE TO RELATED APPLICATION

The present application is a continuation-in-part application of the application of Bijan Amini, U.S. Ser. No. 60/170,281, filed Dec. 10, 1999, entitled Through Tank Level Gauging.

FIELD OF THE INVENTION

The present invention relates generally to utilizing controlled transmissions of electromagnetic (EM) energy through or across materials that have previously been barriers to their penetration to determine the fluid level inside a ferromagnetic or non-ferromagnetic tank, and detect the resistivity of the fluid inside the tank.

BACKGROUND OF THE INVENTION

It has long been possible to measure fluid level within a tank by various methods intrusive to the tank. Prior methods and devices have typically measured pressure or electrical conductivity. The prior methods and devices were typically intrusive, requiring holes for guages, windows of differing materials, dismemberment of tanks, etc. Also, the prior methods and devices had great difficulty in taking measurements with respect to ferromagnetic barrier materials. Many of the prior methods and devices cannot function as a single point level sensor for notifying a controller of the presence or lack of fluid. Further, the prior methods and devices cannot function to measure fluid levels non-intrusively over the full range of a tank or vessel. Still further, the prior methods and devices cannot function to measure fluid levels non-intrusively for both ferromagnetic and non-ferromagnetic tanks or vessels. Further, the prior methods and devices cannot function to determine the resistivity within a tank or vessel in order to determine liquid level, location of the liquid/gas interface, or quality determination of the fluid.

It is, therefore, a feature of the present invention to provide a non-intrusive method and device using electromagnetics to creates a metallic transparency in a ferromagnetic material allowing sensing through the ferromagnetic barrier material.

A feature of the present invention is to provide a single point level sensor for notifying a controller of the presence, a change in or the lack of fluid.

Another feature of the present invention is to provide a method and device that can measure fluid level non-intrusively over the full range of a tank or vessel.

Another feature of the present invention is to provide a method and device that can measure fluid level non-intrusively and functions on non-ferromagnetic tanks or vessels.

Yet another feature of the present invention is to provide a method and device that can determine liquid level, location of the liquid/gas interface, or quality determination of the fluid.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein, a method is provided for creating a non-intrusive device that generates a spectral EM frequency to detect liquid level inside a tank and can identify resistivity within a tank to determine materials in the tank. The present invention applies to both ferromagnetic and non-ferromagnetic tanks. For applications involving ferromagnetic barrier materials, such as, for example, tanks or vessels, the method of the present invention comprises the steps of (a) testing empirically to approximate the conductivity, (b) testing empirically to approximate the permeability, (c) creating a first set of electromagnetic waves adjacent to the material to be measured of a relatively low frequency, (d) impinging the first set of electromagnetic waves on the material for saturating the material, (e) creating a second set of electromagnetic waves having specific constant amplitude of a higher frequency than the first set of electromagnetic waves, the second set of electromagnetic waves for engaging the material and generating a sensing signal having modified characteristics, and (f) receiving the sensing signal through the saturated material such that the modified characteristics of the sensing signal are processed to determine the required information of liquid level and/or liquid type.

Another embodiment of the present invention provides for saturating to a partial level. Saturating to a partial level allows, in a ferromagnetic tank, the signal to both penetrate the tank and travel throughout the tank to utilize the entire tank as a sensing device. At a partial saturation level, the saturation current lowers the magnetic permeability of the ferromagnetic material, e.g., the wall of a tank or the like, enough to allow deeper penetration than expected as well as decreasing the losses of the saturated materials. Therefore, an optimum setting exists that will maximize transfer of electromagnetic energy into the tank walls without forcing excess energy through the tank. In one embodiment of the present invention as applied to non-ferromagnetic tanks, steps "a" through "d" discussed above, are omitted, and, steps e and f transmitted at the appropriate settings provides for electromagnetic penetration of the non-ferromagnetic material. Electromagnetic penetration of the non-ferromagnetic material creates an interaction with the fluid inside the tank. Also, in a non-ferromagnetic level gauge application, the electromagnetic energy is partially transferred into the tank or vessel walls while some energy does penetrate the tank interior. Each embodiment of the present invention can determine a point setting, i.e., trigger the device at a single point, or track incremental changes in level throughout the total height of the tank.

In another embodiment, a method for creating a spectral EM frequency to optimize transfer of energy into a tank by altering the permeability and conductivity is provided. The method comprising the steps of (a) calculating the penetration depth $\delta$ using $$\delta = \left(\frac{1}{e}\right)L$$

and $$\delta = \frac{1}{\sqrt{\sigma \mu_r \mu_o f}}$$

where
$\delta$=penetration depth,
$f$=frequency,
$\mu_r$=relative permeability, and
$\mu_o$=absolute permeability, (b) determining the relationship of frequencies such that $f_6 > f_5 > f_4 > f_3 > f_2 > f_1$, and (c) using the frequencies to determine the thickness of the material.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

Figure 1:
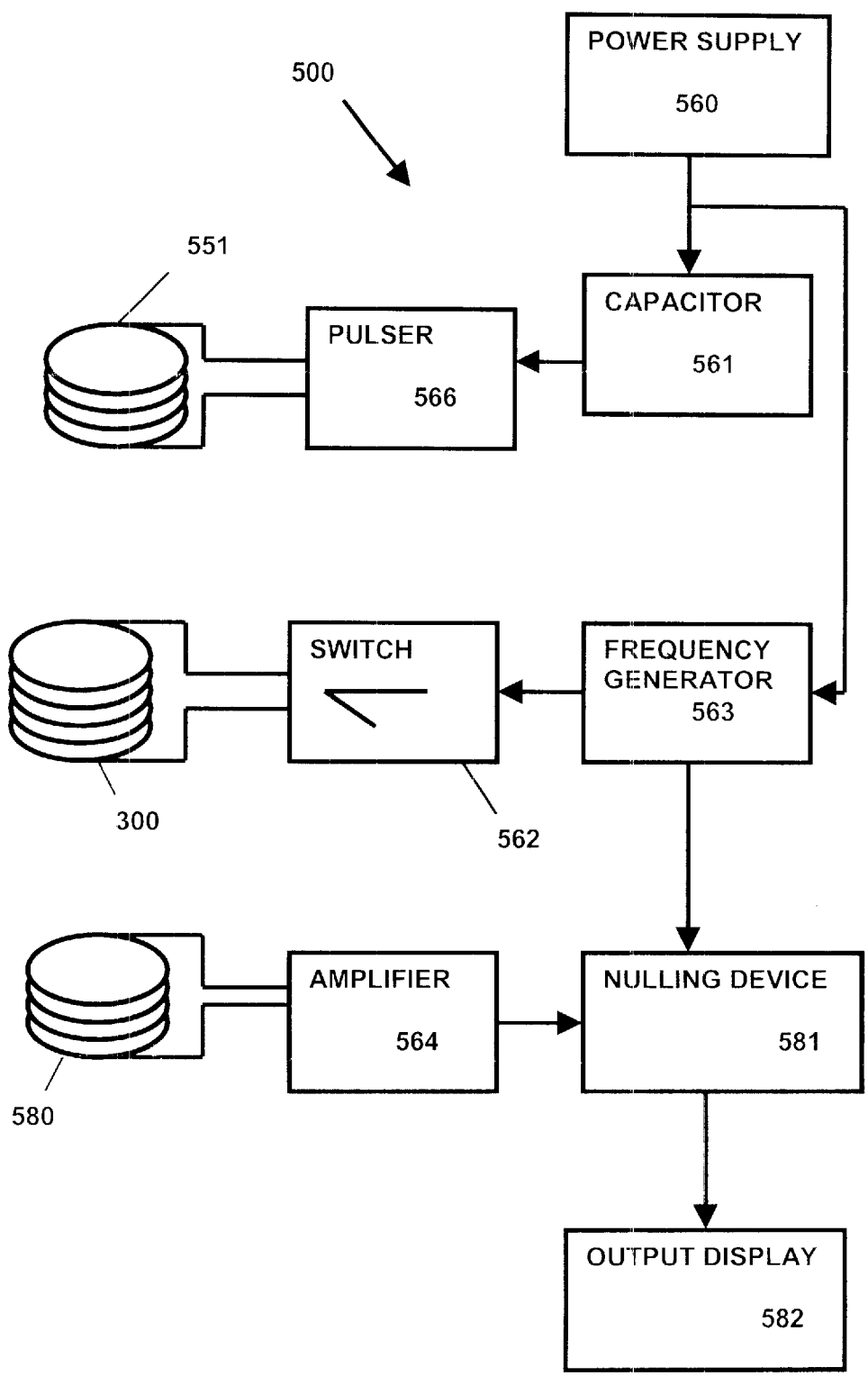
FIG. 1 is a block diagram of one embodiment of a magnetic transparency generator of the present invention.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

It is possible to greatly improve existing methods of measuring liquid level by using an electromagnetic signal transmitted through a barrier material in a non-intrusive method. In a ferromagnetic tank, the tank material permeability and conductivity must be determined so that the effects of permeability and conductivity can be anticipated and adjusted with respect to the measurement. In a non-ferromagnetic tank, the permeability is already near unity and the conductivity of the tank alone contributes to energy losses.

An embodiment of the present invention comprises a method for creating a spectral EM frequency tank level gauge using metallic transparencies in ferromagnetic tanks. Using the metallic transparencies of the present invention with a ferromagnetic tank over the full range of the tank, the initial step in determining tank level with a single device is to create a first set of electromagnetic waves adjacent to or near the material to be measured. The first set of waves may be generated by a permanent magnet, an electromagnet powered by DC current or AC current. The AC powered EM waves will preferably be of a relatively low frequency. The first waves partially saturate the barrier material with the magnetic component. A second set of electromagnetic waves is generated with specific constant amplitude and is monitored using a receiver. The receiver is located adjacent to or near the material to be measured and may be a distance from the transmitter or alternately co-located with the transmitter. The transmitted signal interacts for creating a return signal. The return signal received by an electronic system is nulled. Nulling reduces the return signal to its lowest level. Nulling establishes a baseline with respect to the tank at one extreme, whether empty or full. As the liquid level within the tank changes so does the return signal. Therefore, a transmitted wave of a single frequency can be generated while monitoring the return frequency to determine changes in the response.

In another embodiment the present invention uses partial saturation. The partial saturation of a section of a ferromagnetic material in a tank wall, using a particular frequency, energizes the tank walls for creating an extension of the measurement device. Thus, as the saturation current partially saturates a local area of the tank wall, energy is transmitted both into the tank walls and into the tank. By monitoring and controlling the saturation current, transmitter current, and receiver voltage an optimum setting can be determined to maximize the amount of energy transmitted into the tank walls. By maximizing the energy transmitted into the tank walls, the amount of eddy currents generated within the walls is maximized. The eddy currents generate small magnetic fields within the tank. As the magnetically permeable fluid rises and falls in the ferromagnetic tank, the fluid shorts or dampens the magnetic fields within the fluid filled section of the tank volume, thus, changing the return or received signal.

Another embodiment of the invention with application to ferromagnetic tanks or vessels is a single point sensor. In the single point sensor application, a saturation current is maximized to create the most efficient penetration through the tank walls rather than efficient transfer of energy into the tank walls. Therefore, very few low energy eddy currents are created within the tank wall. Furthermore, the predominate energy being transmitted into the tank in a localized area is determined by the specific design including the transmitter and receiver systems and the saturation coils. In this single point application, the device has a limited height and depth of investigation. As the fluid level enters the investigation area, the electronic signature changes. By monitoring the receiver amplitude and phase, when and were the liquid level crosses the center of the receiver can be very accurately determined. For a single point level sensor outside a ferromagnetic tank using the same transmitter, receiver, and saturation procedures described above, a saturation wave is generated near or close to the barrier material in the area necessary for a single point location (example 95% height). The first set of waves may be generated by a permanent magnet, an electromagnet powered by DC current or AC current. The AC powered EM waves will preferably be of a relatively low frequency.

The first or saturation waves can fully saturate the barrier material with a localized area of the magnetic component. A second set of electromagnetic waves is generated with specific constant amplitude and is monitored using a receiver. The receiver is located adjacent to or near the material to be measured and maybe a distance from the transmitter or alternately co-located with the transmitter. The transmitted signal creates a return signal. The electronic return signal received by the electronic system is nulled, i.e., reduced to its lowest level, establishing a baseline with the tank at one extreme whether empty or full. As liquid level within the tank enters the localized investigation area, the return signal changes. The point at which the amplitude peaks and the phase changes direction or transfers through zero is the level immediately across or within the same place as the centerline of the receiver. Therefore, a transmitted wave of a single frequency can be generated while monitoring the received frequency to determine changes in the response or return signal.

Utilizing full saturation of a section of a ferromagnetic material in a tank wall, at a certain frequency, provides for the tank walls becoming an extension of the measurement device in a localized area. However, one skilled in the art will recognized that the localized area monitored can provide height information within the specific zone of investigation but not over the full height of the tank. Thus, as the saturation current fully saturates a local area of the tank wall, energy is transmitted through the tank wall creating the energized area of investigation. By monitoring and controlling the saturation current, transmitter current and frequency, and receiver voltage, an optimum setting can be achieved to maximize the amount of energy transmitted into the tank. By maximizing the energy transmitted into the tank, the amount of eddy currents generated within a magnetic media inside the tank can be maximized. These eddy currents generate small magnetic fields within the tank wall or media. As the magnetically permeable fluid rises and falls in the ferromagnetic tank, the fluid alters the magnetic fields within the fluid filled section of the tank volume, thus changing the return signal.

Once total saturation occurs additional saturation current has no affect on the received signal. Thus, the transmitted signal is coupled with the metal and the metal is now transparent to the transmitted signal. The current history and the associated received signal, as illustrated in FIGS. 4C, 4D and 4E, provide for full or partial saturation of a localized area. Further, the current history and the received signal information can be used to mathematically determine the permeability and thickness. Once approximations are obtained on either permeability and/or conductivity, the material thickness calculations can be made.

The technique of the present invention for calculating the thickness of a material with unknown permeability and conductivity can be used to further classify various materials and thicknesses such that a general lookup table can be created.

In order to obtain an accurate measurement of permeability and/or conductivity, electronic and geometric nulling are required. Geometric nulling positions the transmitter, receiver and saturation coils in the optimum locations for the particular system designed. Various designs are provided yielding excellent results. Also, an electronic nulling circuit can simultaneously null all of the frequencies at once. Pursuant to practicing the present invention as described herein, one skilled in the art will know and appreciate how to arrange the transmitter, receiver and saturation coils in optimum locations for the particular system being used, and will know and appreciate how to simultaneously null all of the frequencies at once to provide electronic nulling.

FIG. 1 is a block diagram of one embodiment of a magnetic transparency generator 500 of the present invention. The magnetic transparency generator 500 comprises a large coil 551, a small coil 300, and a receiver coil 580. The large coil 551 generates the transparency current The small coil 300 generates the transmitter signal. The receiver coil 580 accepts the returning transmitter signal The large coil 551 for generating the transparency current is engaged with a pulse 566, one or more capacitors 561 and a power source 560. The small coil 300 of the transmitter and the receiver coil 580 are engaged with a switch 562, a frequency generator 563, a low noise amplifier (LNA) 564, an electrical nulling circuit 581 to digital signal processing and an output means 582.

Figure 2:
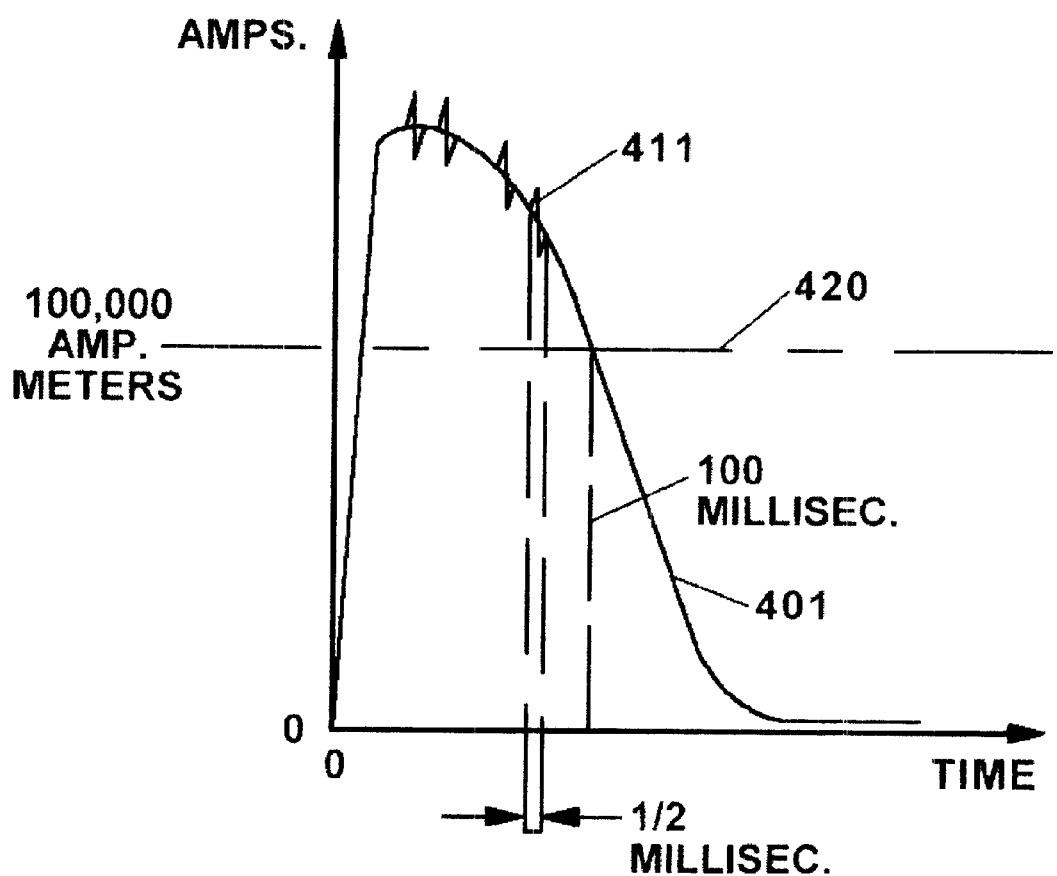
FIG. 2 illustrates a graph of current versus time with respect to the present invention.

FIG. 2 illustrates a graph of current versus time with respect to the present invention. FIG. 2 illustrates three significant features in practicing the present invention: the current level required for saturation 420, the higher frequency sensing signal 411 and the lower frequency transparency signal 401. The higher frequency sensing signal 411 is imposed on the lower frequency transparency signal 401. FIG. 2 illustrates as spikes 411 the higher frequency oscillating electromagnetic wave of the sensing signal 411 disposed along a lower frequency oscillating transparency current 401. In one embodiment of the present invention, the sensing signal 411 may be transmitted only during the duration of each cycle of the oscillating transparency current 401 that is above the level 420 required for saturation. Among other advantages, the latter embodiment minimizes energy consumption. In the latter embodiment, it is possible to have multiple sensing signal transmissions 411 during each phase that the transparency current 401 is above the saturation level 420.

The transparency current 401 may not achieve the level of current necessary to saturate the targeted area of the EM barrier material. However, the distinctively higher frequency sensing signals 411 will couple, i.e., penetrate, into the EM barrier or, alternatively, be of sufficient magnitude to saturate a volume region of transparency or partial transparency when combined with the transparency current, and therefore, directly penetrate through the barrier material. In another embodiment, the transparency current may be generated from at least one permanent magnet, a low frequency AC current or a direct current DC electromagnetic device.

Illustrated schematically as an apparatus in FIG. 1 and conceptually in FIG. 2, the higher frequency sensing signal 411 may be generated by a transmitter, comprised of a smaller coil 300 of conductive material, powered by alternating current and at a controlled frequency, wrapped upon or near the larger coil 551. The larger coil 551 generates the transparency current which in turn generates the transparency field. It is wrapped with conductive material and powered either by DC current or an oscillating current. Preferably, the transmitter current is at a higher frequency than the transparency current. It is preferred that the frequency of the sensing signal be at least a multiple of 10 greater than the frequency of the transparency signal. As discussed above, the higher sensing frequency allows, for example, 10 wavelengths of measurement before the transparency is closed.

In FIG. 2, the high frequency sensing signal 411 is illustrated being pulsed at less than 0.5 millisecond rates. If the lower frequency transparency current 401 generated by the larger coil 551, is pulsed or activated "on" for 10 milliseconds 430, there is sufficient time for twenty sensing signals (e.g., with a wavelength of only 0.5 millisecond) to go out to a near object and take 10 wavelengths of measurements during the "on" pulse of the transparency current. During this 10 millisecond pulse, the transparency current will exceed the saturation energy level 420. The higher frequency signal 411 from the transmitter coil 300 is being pulsed at a 0.5 millisecond rate so that 20 sensing signals will be available during a 10 millisecond pulse of the transparency signal 401.

For most applications, a power source of 300 watts or less is sufficient to create the signal and saturation. For thicker material, strong pulses and signals may be generated by utilizing the charge storing capacitors 561. The capacitors 561 are slowly charged then quickly discharged through a switch contact and then through the low impedance large coil 551. At the same time, the higher frequency small signal coil 300 is pulsed.

Figure 3:
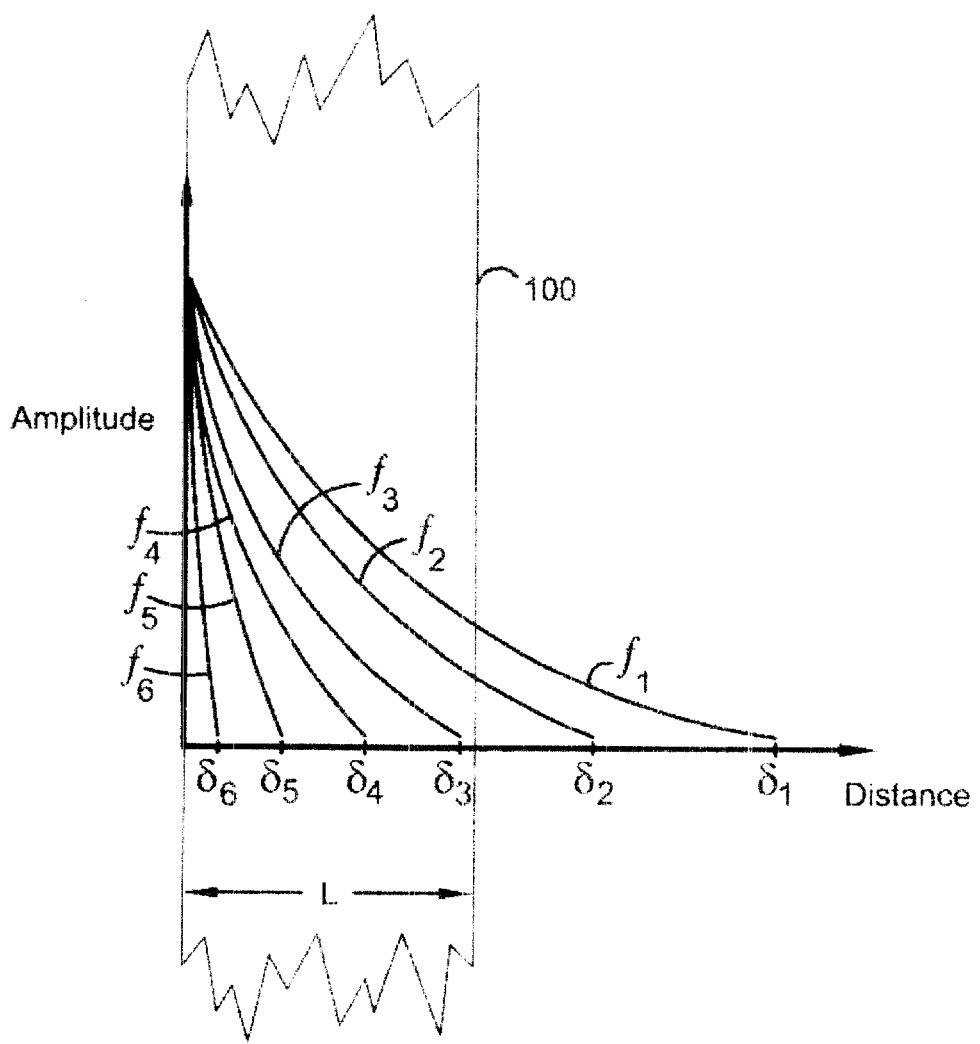
FIG. 3 illustrates the relationship between signal frequency and penetration depth for a cross-section of a piece of metal with a conductivity, a permeability and several imposed frequencies, $f_x$, for the present invention.

FIG. 3 illustrates the relationship between signal frequency and penetration depth for a cross-section of a piece of metal with conductivity, permeability and several imposed frequencies, $f_x$, for the present invention. For a wave of constant amplitude and varying frequency, and a metal with the same permeability and conductivity, it is known by skin depth theory that a lower frequency penetrates deeper than a higher frequency. Therefore, one can find an optimum frequency range that can characterize the metal conductivity. For constant length L and varying frequencies, the penetration depth $\delta$ is:

$$\delta = \left(\frac{1}{e}\right) L$$

and $$\delta = \frac{1}{\sqrt{\sigma \mu_r \mu_o f}}$$

where
 $\delta$=penetration depth,
 $f$=frequency,
 $\mu_r$=relative permeability, and
 $\mu_o$=absolute permeability.
In FIG. 3, the relationship of frequencies is $$f_6 > f_5 > f_4 > f_3 > f_2 > f_1.$$

Figure 4:
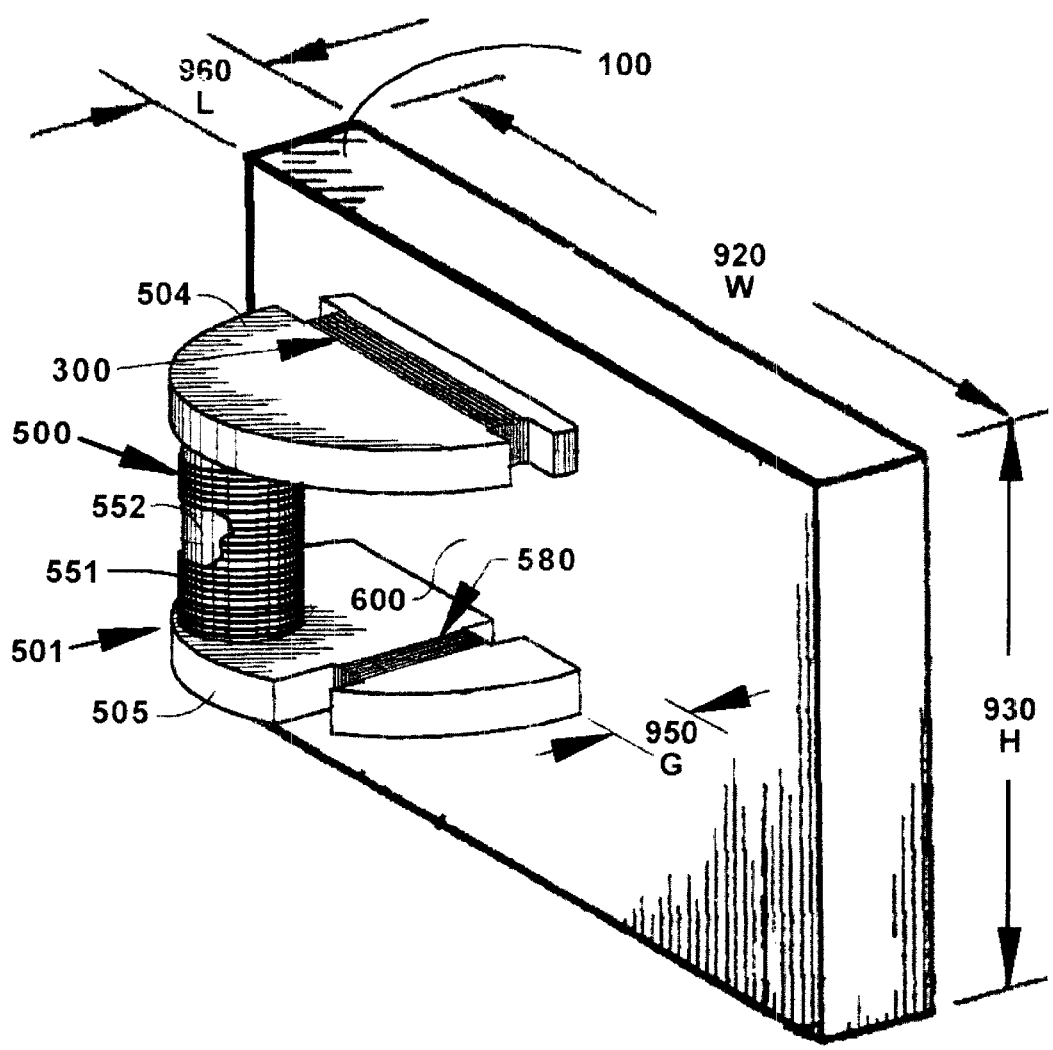
FIG. 4 illustrates the flux circuit core of one embodiment of the magnetic transparency generator used to generate the transparency current required in practicing the present invention.

FIG. 4 illustrates one embodiment of a magnetic transparency generator 500 used to generate the transparency current required in practicing the present invention. The magnetic transparency generator 500 provides for containing flux lines to completely saturate the intended barrier material 100 volume region. Also, FIG. 4 illustrates one embodiment of the flux circuit core 501 for use with the present invention. The flux circuit core 501 comprises a top flange 504, a bottom flange 505 and a core 552. The core 552, upon which the coils of the electromagnet are wrapped, is located between the top flange 504 and bottom flange 505. The tank wall comprises the barrier material 100. The complete magnetic transparency generator 500 incorporates the flux circuit core 501 for providing a transparent volume region that is illustrated having a width W 920, a height H 930 and a thickness L 960. The barrier volume region may be termed the target material. It is appreciated that the transmitter coils 300, the receiver coils 580 and the transparency coil 551 are in positions of geometric nulling with respect to the magnetic transparency generator 500 illustrated.

Figure 4A:
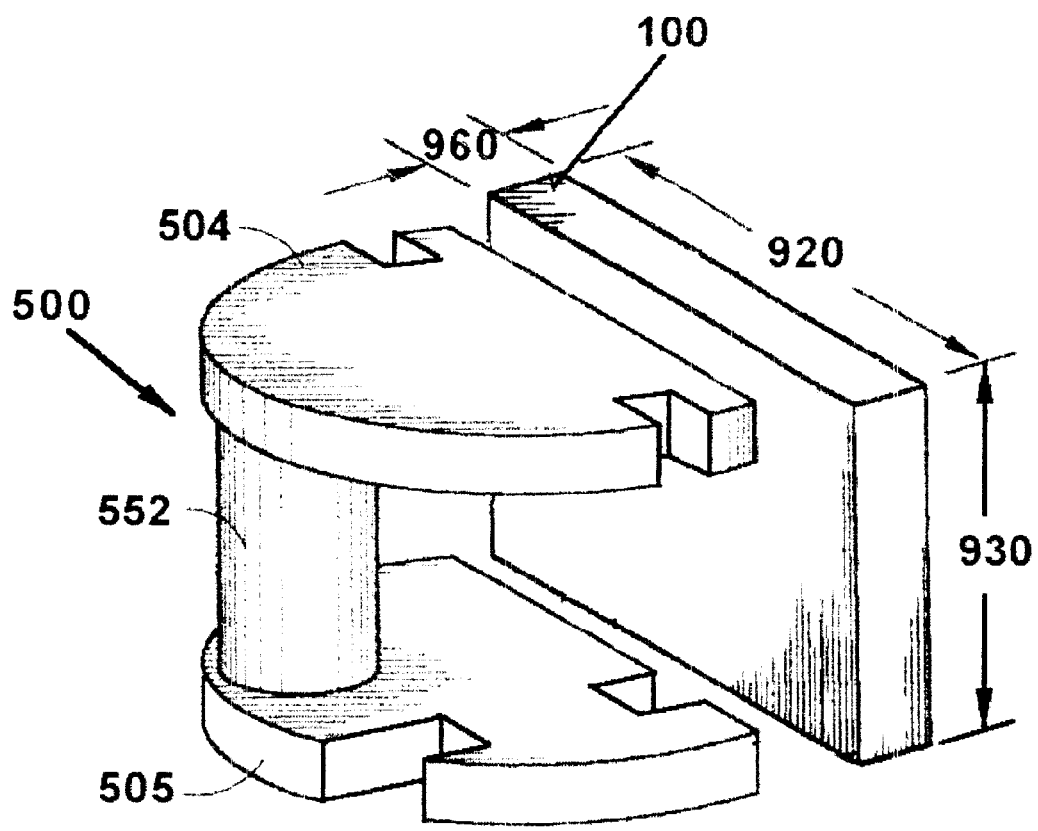
FIG. 4A illustrates one embodiment of a flux circuit core for use with the present invention.

FIG. 4A illustrates one embodiment of the flux circuit core 501 for use with the present invention. The flux circuit core 501 comprises a top flange 504, a bottom flange 505 and a core 552.

Figure 4B:
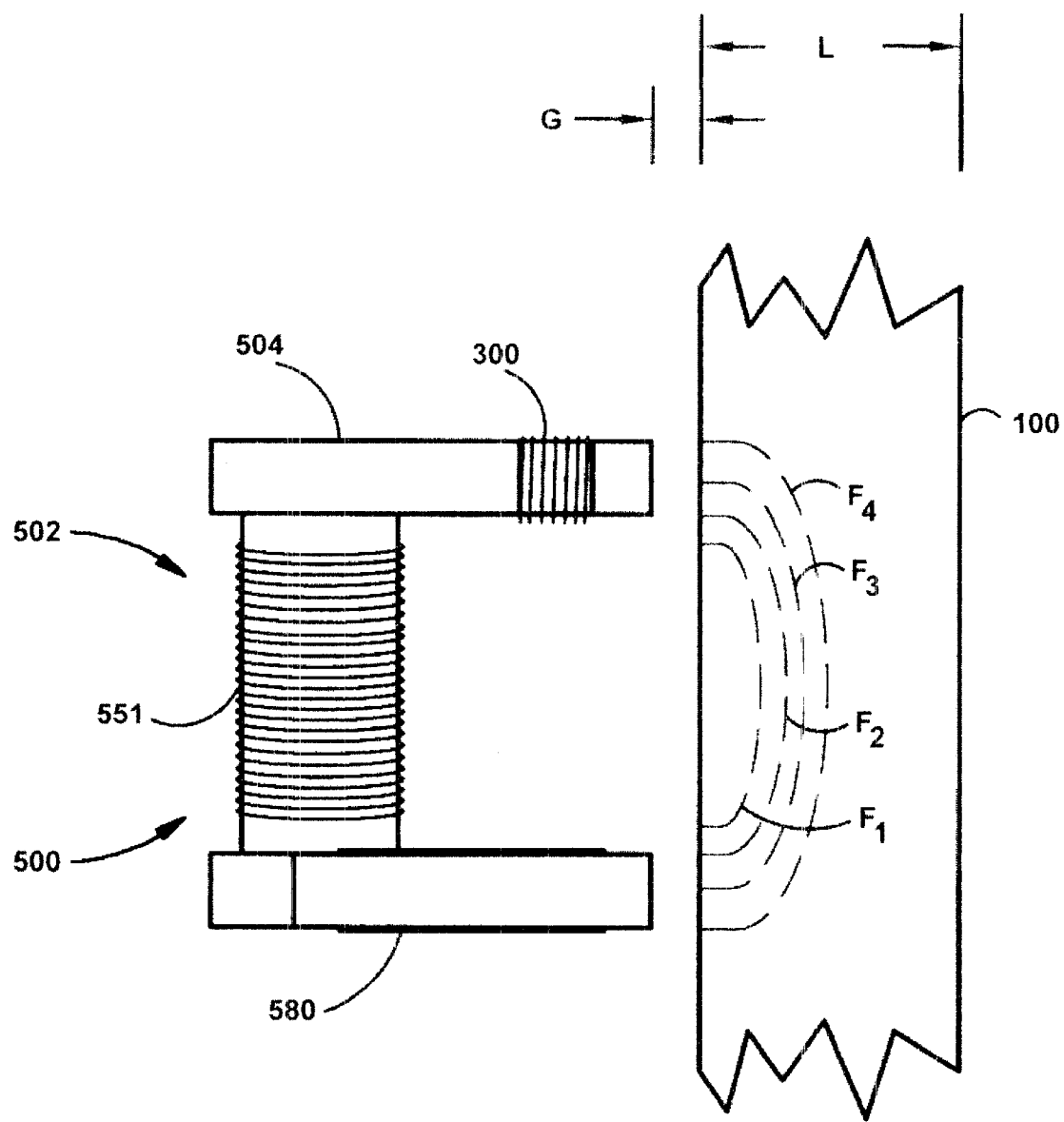
FIG. 4B illustrates one embodiment of a magnetic circuit for use with the present invention.
Figure 4C:
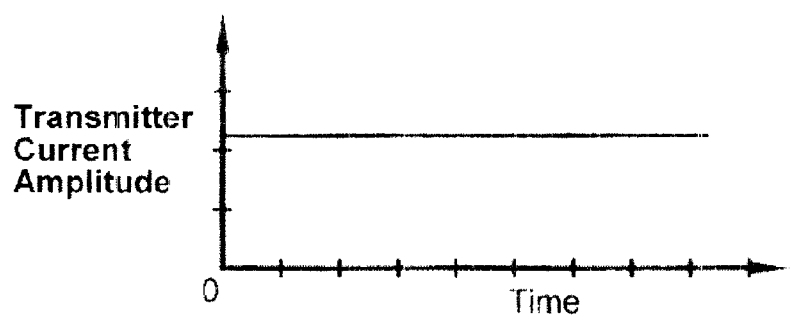
FIGS. 4C, 4D and 4E illustrate the relationship between the transmitter current amplitude (FIG. 4C), the saturation current amplitude (FIG. 4D), and the receiver current amplitude (FIG. 4D) with respect to the magnetic circuit illustrated in FIG. 4B.
Figure 4D:
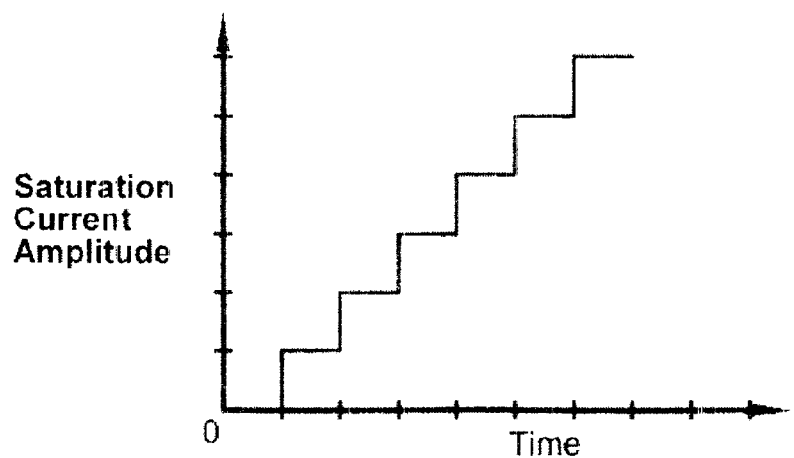
Figure 4E:
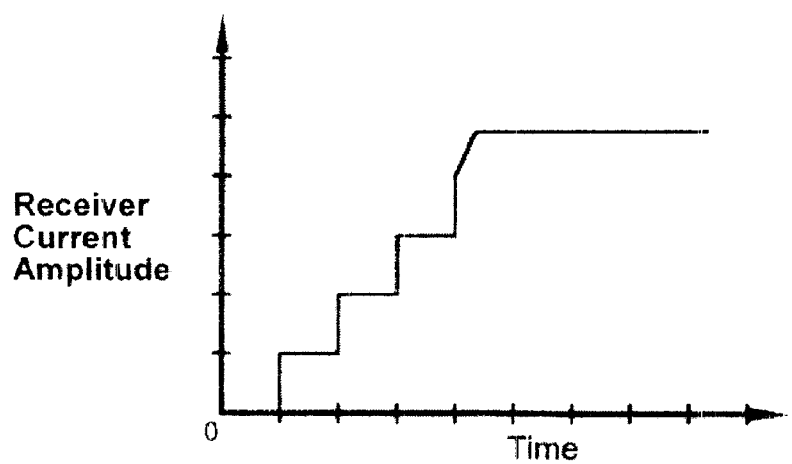

FIG. 4B illustrates one embodiment of the magnetic circuit 502 for use with the present invention. The magnetic circuit 502 comprises the saturation coil 551, the transmitter coil 300, the receiver coil 580 and the barrier material 100. The magnetic transparency generator 500 is disposed from the barrier material 100 by a gap G. The barrier material 100 has a width L. The magnetic circuit 502 operates by energizing the saturation coil 551 for saturating the barrier material 100, transmitting a sensing signal from the transmitter coil 300, and receiving a response via the receiving coil 580. The relative penetration is caused by the change in the saturation current. Thus, as the saturation current increases from $i_1$, to $i_2$, to $i_3$, to $i_4$ then the penetration depth increases from $\delta_1$, to $\delta_2$, to $\delta_3$, to $\delta_4$, respectively. FIG. 4B illustrates the incremental increase in penetration by the field lines $F_1$, $F_2$, $F_3$ and $F_4$. Also, consideration of the cross-sectional area of each component of the magnetic circuit 502 is required to assure that no component goes into total saturation for a specific power requirement necessary to drive the EM wave across the air gap G.

FIGS. 4C, 4D and 4E illustrate the relationship between the transmitter current amplitude, the saturation current amplitude, and the receiver current amplitude with respect to the magnetic circuit 502 illustrated in FIG. 4B. FIG. 4C illustrates that the transmitter current amplitude maybe constant over time. FIG. 4C shows that the saturation current amplitude is increased as a step function over time. With the transmitter current amplitude held constant over time and the saturation current amplitude increased as a step function over time, the receiver current amplitude will increase as a step function congruent with the saturation current amplitude up to and until the barrier material is in a state of total saturation. When the barrier material is in a state of total saturation, the receiver current amplitude is at a maximum and cannot increase because maximum penetration has been achieved.

Figure 5:
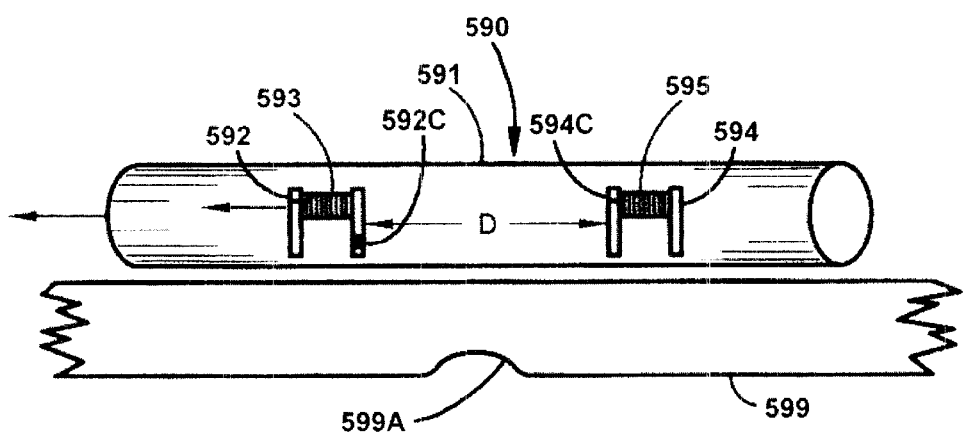
FIG. 5 illustrates one embodiment of a bistatic magnetic transparency generator of the present invention.

FIG. 5 illustrates one embodiment of a bistatic magnetic transparency generator 590 of the present invention. Using the bistatic magnetic transparency generator 590 shown in FIG. 5, the permeability is driven to unity. Electromagnetic waves are transmitted by the transmitter 592 at different frequencies and monitored with the receiver 594. A metallic transparency is created by generating a saturation of the barrier material 599. An electromagnetic wave is generated using the transmitter 592 at a preset frequency and constant amplitude. Assuming the first frequency is within the detectable frequency range, the frequency is increased incrementally until the received signal is lost. See FIGS. 4C–E. The last frequency detected prior to losing the received signal determines the maximum frequency detectable in a certain piece of barrier material 599 of constant thickness, permeability, and conductivity. See FIG. 4E. Using the data and information received in empirical testing for permeability, the material properties and thickness can be very precisely calculated.

In FIG. 5, the bistatic magnetic transparency generator 590 comprises a housing 591, a transmitter 592 and a receiver 594. The transmitter 592 and the receiver 594 are displaced by a distance D. The transmitter 592 includes a transmitter coil 592C and a saturation magnet 593. The receiver 594 includes a receiver coil 594C and a saturation magnet 595. The bistatic magnetic transparency generator 590 is in operative association with a barrier material 599 having a defect 599D. It can be appreciated by those skilled in the art that in the bistatic configuration illustrated in FIG. 5 the distance D must be sufficiently small to detect the defect 599A. Such that the accuracy is limited by the mass to be evaluated and the displacement distance D.

Figure 6:
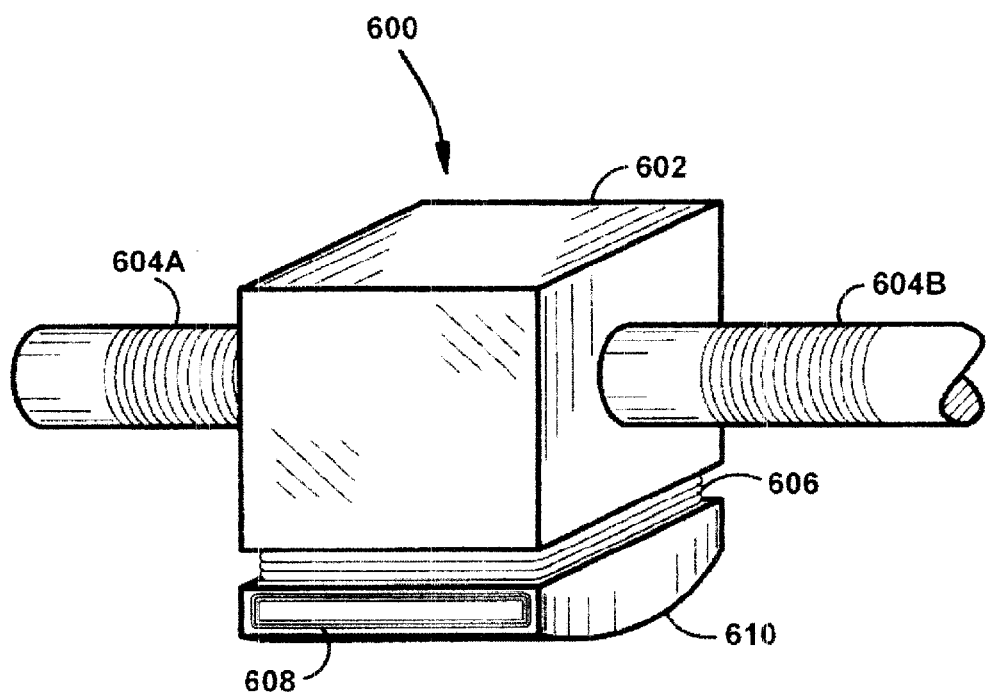
FIG. 6 illustrates one embodiment of a magnetic transparency generator of the present invention in operative association with a culminator.

FIG. 6 illustrates one embodiment of a magnetic transparency generator 600 of the present invention in operative association with a culminator 602. The transmitter 606 and the receiver 608 are both on the same culminator 602. The displacement distance D between the transmitter 606 and the receiver 608 is essentially zero. The displacement distance D is essentially zero because of the close configuration of the transmitter 606 and the receiver 608. The intensity of the frequencies received will show the metal thickness. For example, if all the higher frequencies are attenuated, the metal is thick. If all the high frequencies are detected with little attenuation of the low frequencies, the metal is thin. For a given power, the displacement distance D between the transmitter 606 and the receiver 608 determines the resolution of the thickness measurement. The resolution effects the size of the defect measurable.

Figure 7:
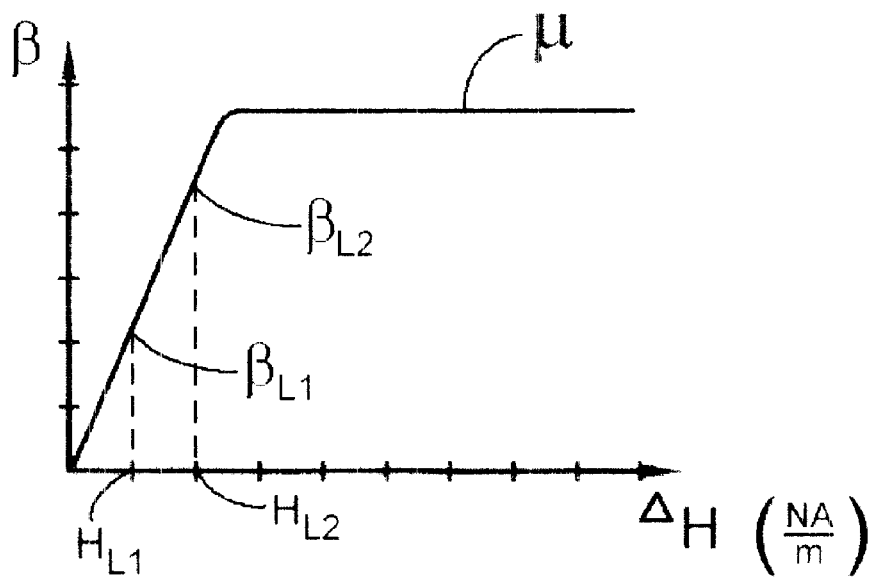
FIG. 7 illustrates the relationship between the flux field β and the change in H (ΔH) in turns-amp/meters.

FIG. 7 illustrates the relationship between the flux field $\beta$ and the change in H ($\Delta$H) in turns-amp/meters. The permeability $\mu$ is plotted. For the relationship between the flux field $\beta$ and $\Delta$H, the function defining the permeability $\mu$ remains the same. Although the function defining the permeability $\mu$ remains the same the value of $\Delta$H for thinner materials moves up the curve faster. Thus, incremental changes in H create a faster advancement up the permeability curve toward saturation. For example, a given $H_{L1}$ corresponds to the value of $\beta_{L1}$ and a corresponding $H_{L2}$ corresponds to the value of $\beta_{L2}$. Thus, the value for L2 moves faster up the permeability $\mu$ curve than the value for L1.

Figure 8:
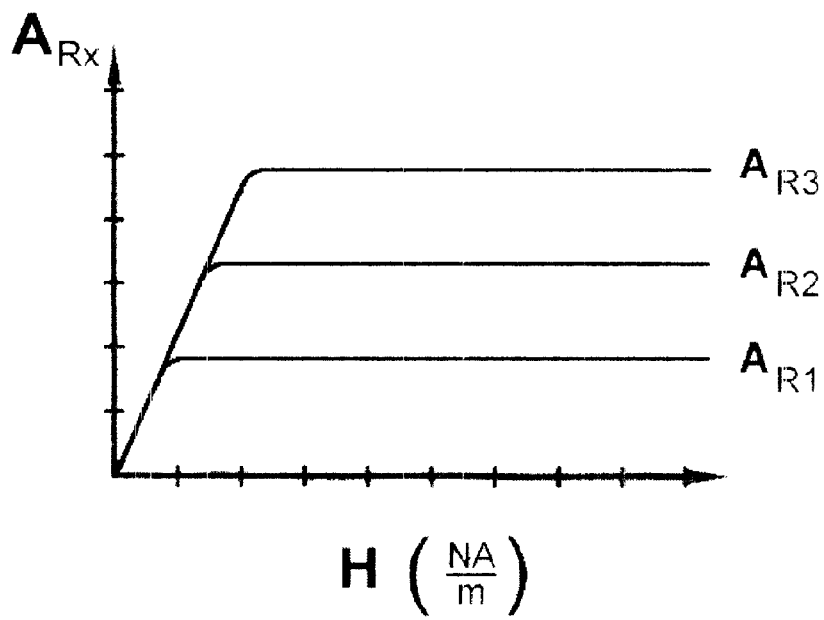
FIG. 8 illustrates the relationship between the receiver amplitude $A_{Rx}$ and H in turns-amp/meters.

FIG. 8 illustrates the relationship between the receiver amplitude $A_{Rx}$ and H in turns-amp/meters. As in FIG. 7, the slope of the curve in FIG. 8 is related to the permeability $\mu$. However, the receiver amplitude $A_{Rx}$ reaches a different maximum value depending on the thickness of the material. For thinner materials, the receiver amplitude $A_{Rx}$ reaches its maximum value at a lower amplitude $A_{Rx}$. For thicker materials, the receiver amplitude $A_{Rx}$ reaches its maximum value at a higher amplitude $A_{Rx}$. FIG. 8 illustrates a thinner material having a maximum at $A_{R1}$, a thicker material having a maximum at $A_{R3}$, and an intermediate thickness material having a maximum at $A_{R2}$.

Figure 9:
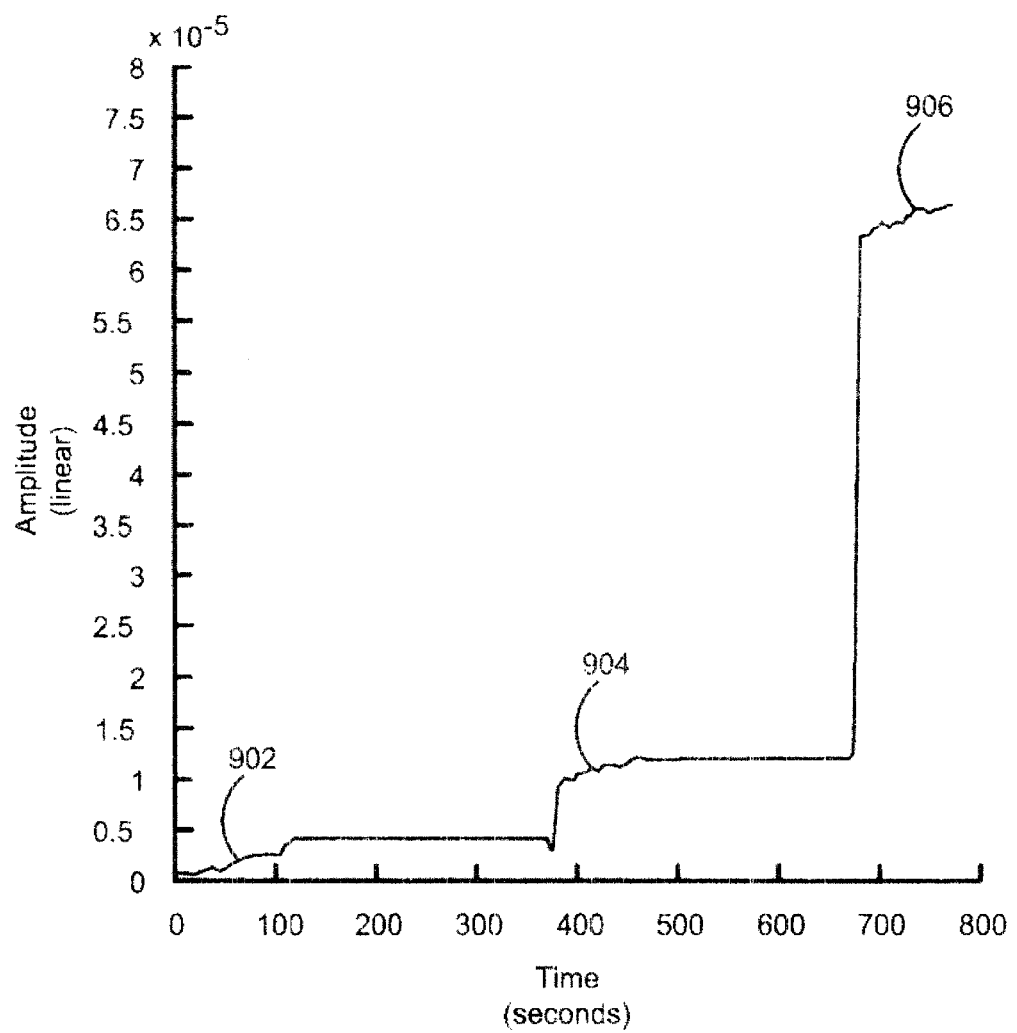
FIG. 9 is a graph of amplitude versus time for a bistatic configured magnetic transparency generator of the present invention.

FIG. 9 is a graph of amplitude versus time for a bistatic configured magnetic transparency generator of the present invention. The frequency is held constant (fixed) and the material is varied. The bistatic magnetic transparency generator was nulled using copper 902. Thereafter, the copper was replaced with brass causing the amplitude to vary from the original nulled position 902 to a new position 904. Since brass and copper have related properties, the dislocation 904 from the copper nulled position 902 is small. However, when the brass is replaced with aluminum the amplitude 906 varies significantly from the original nulled position 902. Aluminum and copper have significantly different physical characteristics.

Figure 10A:
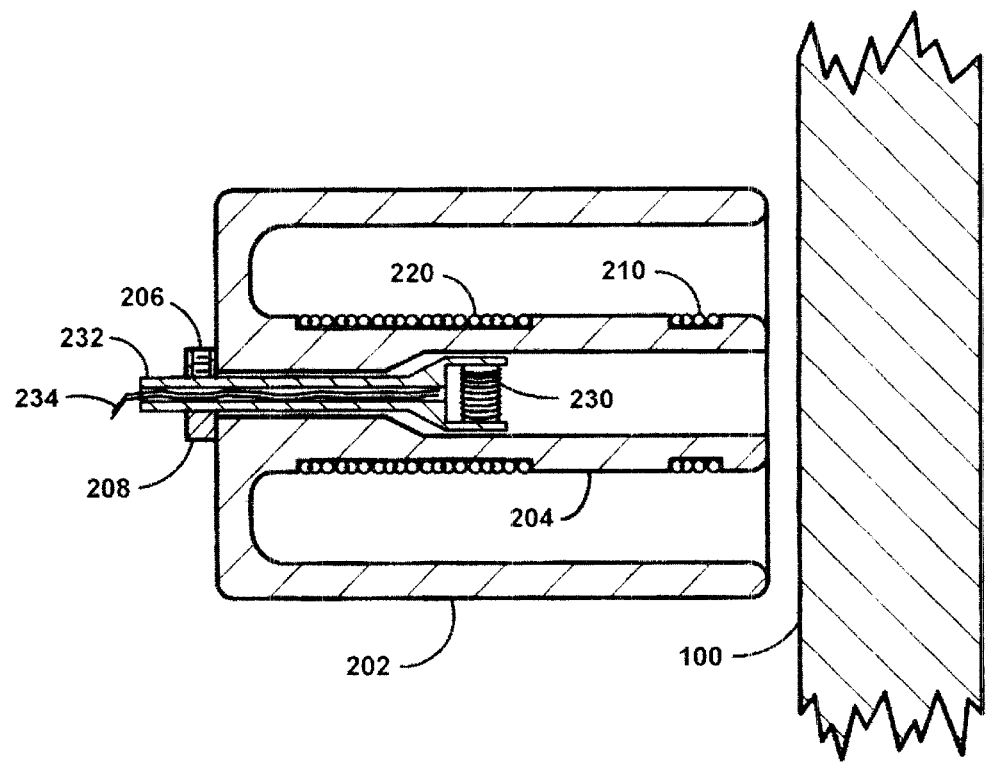
FIG. 10A illustrates an embodiment of a magnetic transparency generator used to generate a transparency with respect to a material for practicing the present invention as could be adapted in FIG. 10.
Figure 10:
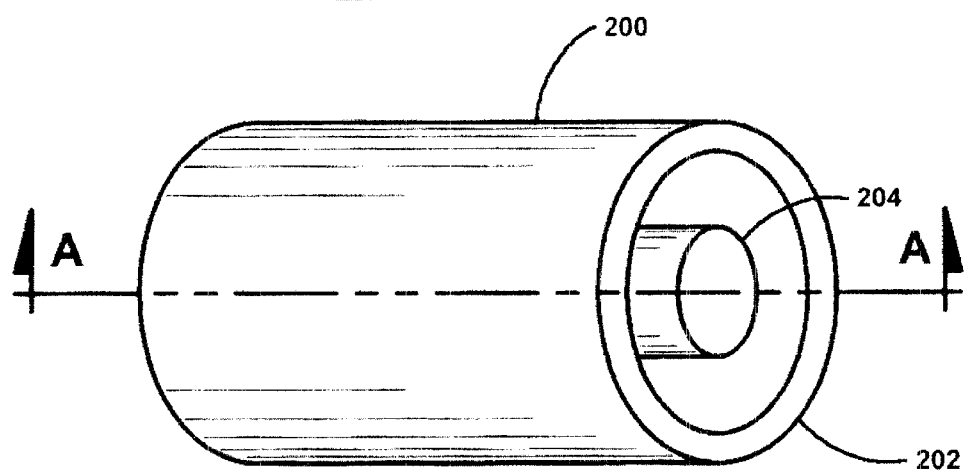
FIG. 10 illustrates another embodiment of a magnetic transparency generator used to generate a transparency in practicing the present invention.

FIG. 10 illustrates another embodiment of a magnetic transparency generator 200 used to generate a transparency in practicing the present invention. The magnetic transparency generator 200 comprises an outer cylindrical portion 202 and an inner cylindrical portion 204. The transmitter, receiver and saturation coils are disposed on, in or around the outer cylindrical portion 202 and the inner cylindrical portion 204.

FIG. 10A illustrates an embodiment of a magnetic transparency generator 200 used to generate a transparency with respect to a material 100 for practicing the present invention as could be adapted in FIG. 10. A transmitter coil 210 is disposed at the remote end of the of the outside diameter of the inner cylindrical portion 204 of the magnetic transparency generator 200. A saturation coil 220 is disposed at the inner end of the of the outside diameter of the inner cylindrical portion 204 of the magnetic transparency generator 200. A receiver coil 230 is disposed within the inside diameter of the inner cylindrical portion 204 of the magnetic transparency generator 200. The receiver coil 230 can be located at different positions using a shaft 232 which telescopes within the inside diameter of the inner cylindrical portion 204 of the magnetic transparency generator 200. The telescoping shaft 232 can also rotate using a setscrew adjustment 206 and a setscrew housing 208. Also, wiring 234 can be channeled through the shaft 232.

Figure 10B:
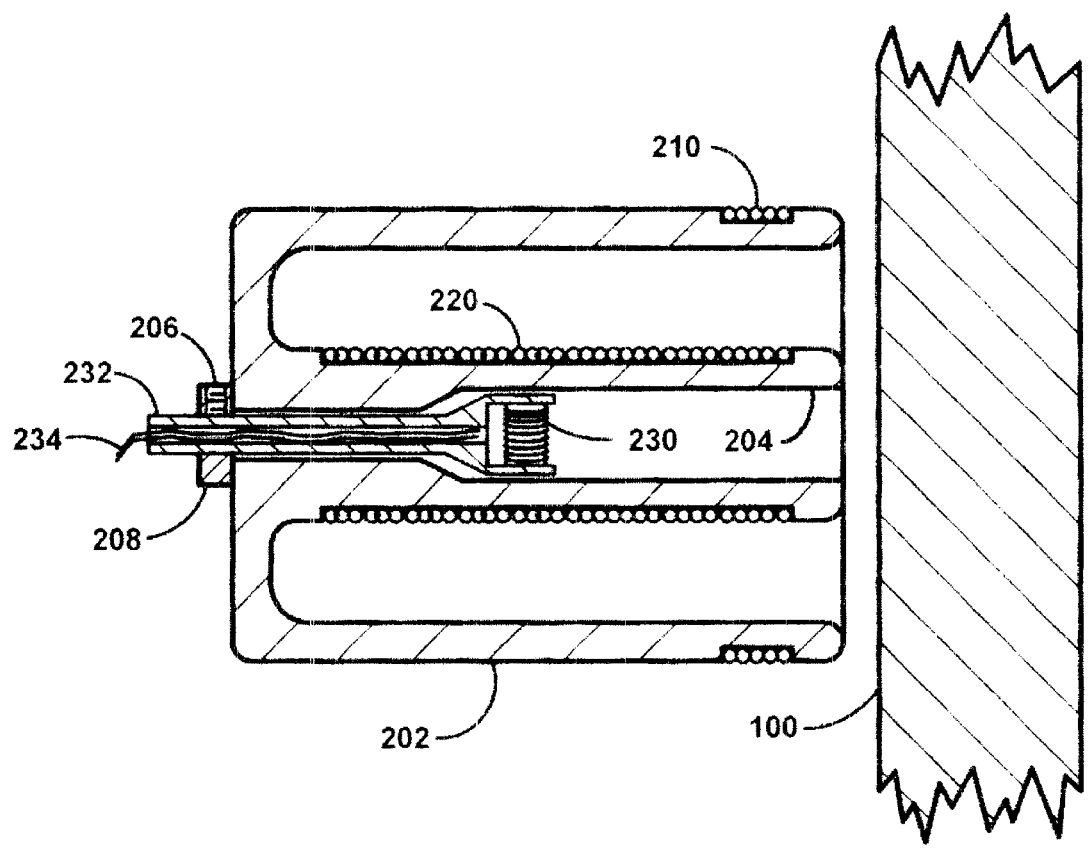
FIG. 10B illustrates another embodiment of a magnetic transparency generator used to generate a transparency with respect to a material for practicing the present invention as could be adapted in FIG. 10.

FIG. 10B illustrates another embodiment of a magnetic transparency generator 200 used to generate a transparency with respect to a material 100 for practicing the present invention as could be adapted in FIG. 10. A transmitter coil 210 is disposed at the remote end of the outside diameter of the outer cylindrical portion 202 of the magnetic transparency generator 200. A saturation coil 220 is disposed along the outside diameter of the inner cylindrical portion 204 of the magnetic transparency generator 200. A receiver coil 230 is disposed within the inside diameter of the inner cylindrical portion 204 of the magnetic transparency generator 200. The receiver coil 230 can be located at different positions using a shaft 232 which telescopes within the inside diameter of the inner cylindrical portion 204. The telescoping shaft 232 can also rotate using a setscrew adjustment 206 and a setscrew housing 208. Also, wiring 234 can be channeled through the shaft 232.

Figure 11:
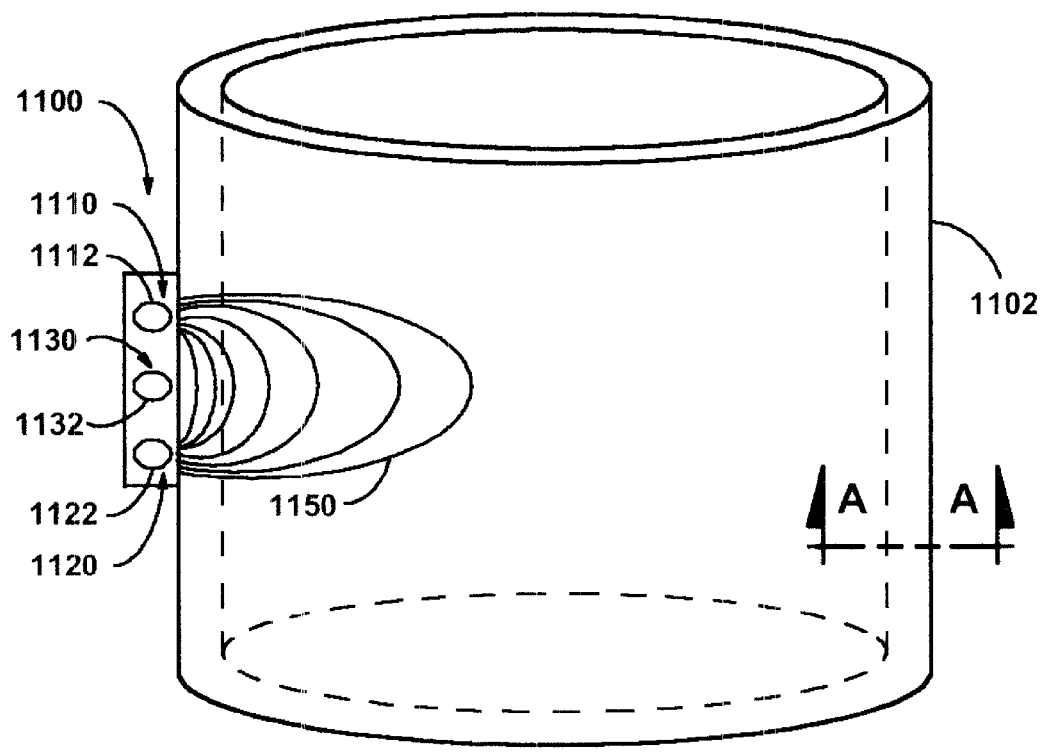
FIG. 11 illustrates one embodiment of a single point magnetic level gauge practicing the present invention as used to generate a transparency with respect to a ferromagnetic tank.

FIG. 11. illustrates an embodiment of a single point magnetic level gauge sensor 1100 used to generate a transparency with respect to a ferromagnetic tank 1102. A transmitter Tx 1110 has a coil 1112 located near the ferromagnetic tank wall 1102. A DC saturator and associated saturation coil 1132 is positioned between the transmitter Tx 1110 and a receiver Rx 1120 having a receiver coil 1122. The receiver coil 1122 is located near the ferromagnetic tank 1102 and oriented with its centerline perpendicular to the centerline of the transmitter coil 1112. The saturation coil 1132 is energized and maintained at a constant voltage necessary to saturate a localized section of the ferromagnetic tank wall 1102, thus creating a low permeability area as required to couple a transmitted signal. The transmitter coil 1112 is excited at a certain constant frequency while the receiver coil 1122 monitors any received signals. The received signal is nulled or reduced to a minimum amount of electronic noise with respect to the tank condition, whether full or empty.

As the fluid level changes near the fluid interface zone of influence, the amplitude and phase of the received signal changes. The point at which the received signal phase changes is the centerline of the receiver Rx 1120. By real time monitoring of the phase change, the point level determination is achieved. One application of a device in this configuration is a high level or low level sensor for storage tanks. The saturation coil 1132 setting determines the amount of transparency created through which the transmitted signal will penetrate.

Figure 11A:
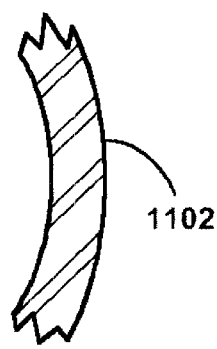
FIG. 11A is a cross-section of the ferromagnetic tank illustrated in FIG. 11 along the section line A—A showing no eddy currents within the wall of the non-ferromagnetic tank.

FIG. 11A is a cross-section of the ferromagnetic tank 1102 illustrated in FIG. 11 along the section line A—A showing no eddy currents within the wall of the non-ferromagnetic tank. FIG. 11A illustrates a cross-section of a ferromagnetic tank wall 1102 across the tank from the sensor 1100. As shown in FIG. 11A, no significant eddy currents exist away from the sensor 1100.

Figure 12:
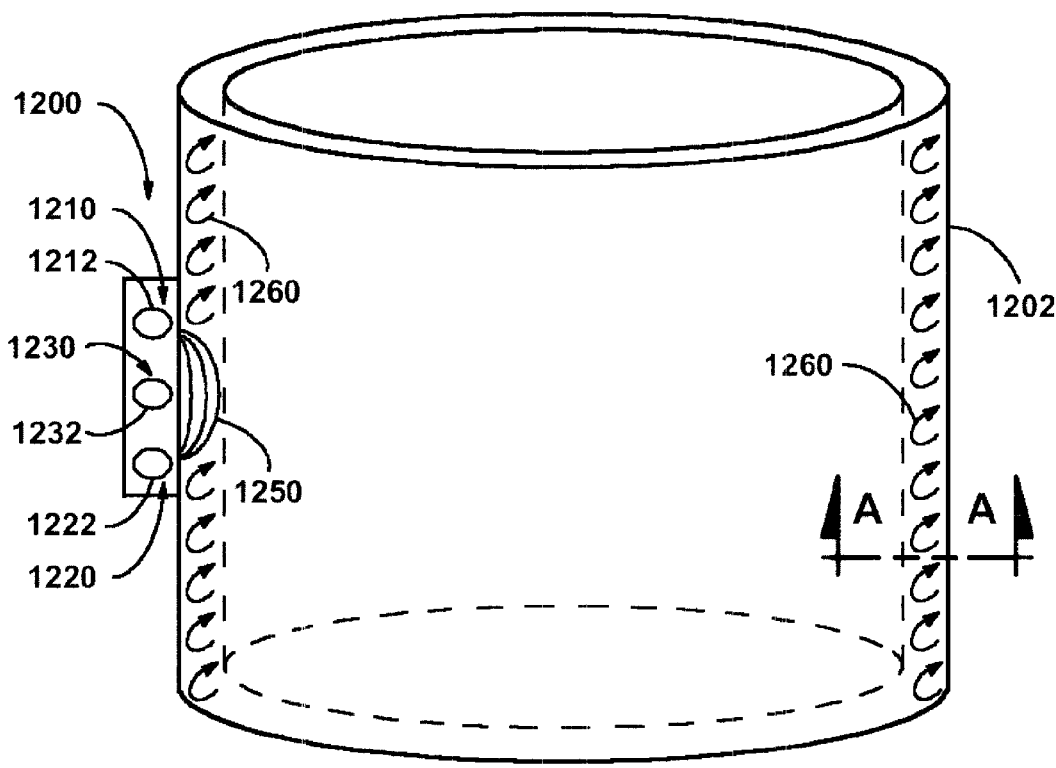
FIG. 12 illustrates an embodiment of a full range magnetic level gauge used to generate an accurate measurement over the full range of a ferromagnetic tank.

FIG. 12 illustrates an embodiment of a full range magnetic level gauge sensor 1200 used to generate an accurate measurement over the full range of a ferromagnetic tank 1202. FIG. 12 illustrates an embodiment of a full range magnetic level gauge sensor 1200 used to generate a transparency with respect to a ferromagnetic tank 1202. A transmitter coil 1212 located near the ferromagnetic tank wall 1202. A saturation coil positioned located between a transmitter coil 1212 and a receiver coil 1222. A receiver coil 1222 located near the ferromagnetic tank 1202 and oriented with centerline perpendicular to the centerline of the transmitter coil 1212. The saturation coil 1232 is energized and maintained at a constant voltage necessary to partially saturate a localized section of the ferromagnetic tank wall, thus creating a low permeability area required to couple the transmitted signal. The transmitter coil 1212 is excited at a certain constant frequency while the receiver coil 1222 monitors any received signals. The received signal is nulled or reduced to a minimum amount of electronic noise with respect to the tank condition, whether full or empty. As the fluid level changes in the tank, the fluid influences the amplitude and phase of the received signal. By real time precise monitoring of the signal, the full range level determination is achieved. One application of a device in this configuration is a full range fluid level sensor used in tanker cars for rapid discharge of fluid from the tank. The saturation coil 1232 setting determines the amount of transparency created through which the transmitted signal will penetrate. If the saturation current is too high, the signal penetrates the tank wall and eddy currents are not created within the wall. If the saturation current is too low, the signal will not penetrate the exterior of the tank wall which will also prevent eddy currents developing within the tank wall.

Figure 12A:
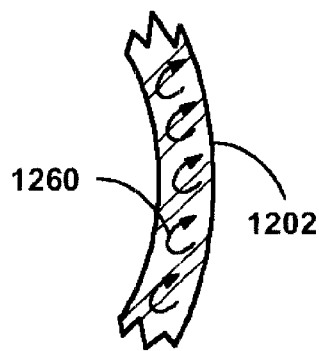
FIG. 12A is a cross-section of the ferromagnetic tank illustrated in FIG. 12 along the section line A—A showing eddy currents within the walls of a ferromagnetic tank.

FIG. 12A is a cross-section of the ferromagnetic tank illustrated in FIG. 12 along the section line A—A showing eddy currents within the walls of a ferromagnetic tank. FIG. 12A illustrates a cross-section of a ferromagnetic tank 1202 wall across the tank from the embodiment of the sensor 1200. As shown in FIG. 12A, significant eddy currents exist away from the sensor 1200. Thus, the tank walls act as an extension of the sensor 1200 to allow full range sensing of the ferromagnetic tank.

Figure 13:
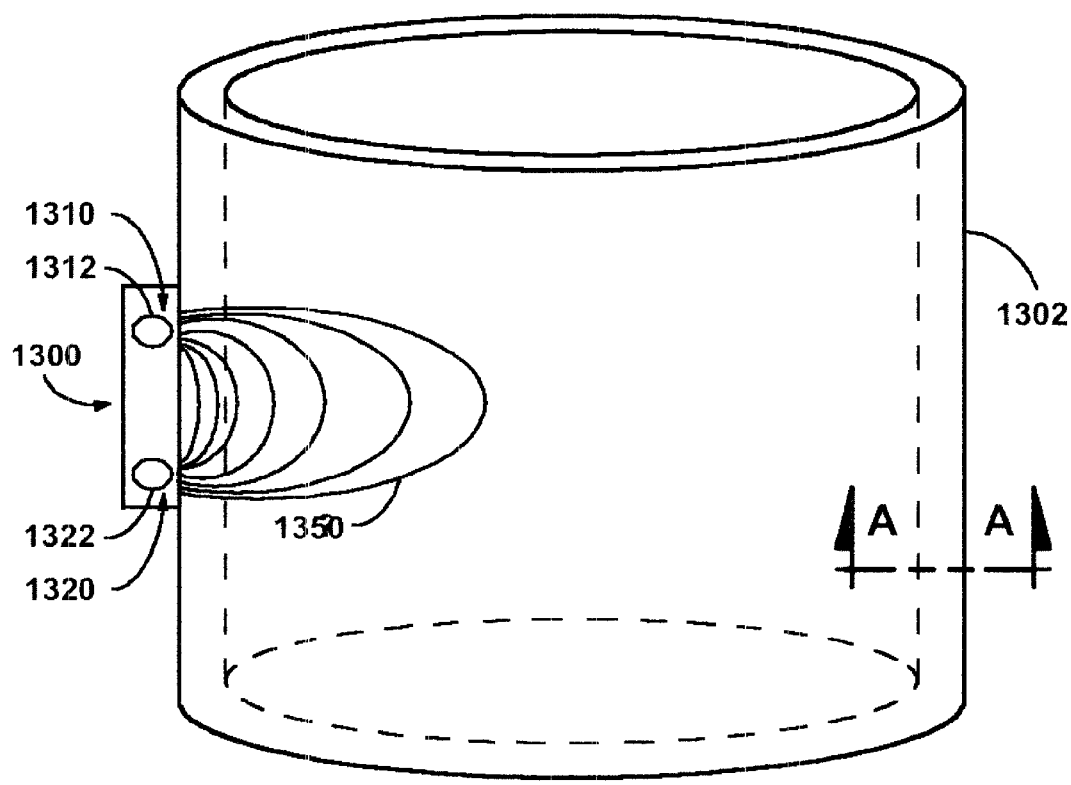
FIG. 13 illustrates an embodiment of a single point magnetic level gauge as practiced by the present invention as used to generate a localized level sensor with respect to a non-ferromagnetic tank.

FIG. 13 illustrates an embodiment of a single point magnetic level gauge sensor 1300 as practiced by the present invention as used to generate a localized level sensor with respect to a non-ferromagnetic tank. FIG. 13. illustrates an embodiment of a single point magnetic level gauge sensor 1300 used to generate a transparency with respect to a non-ferromagnetic tank. A transmitter coil 1312 located near the non-ferromagnetic tank wall 1302. A receiver coil 1322 located near the ferromagnetic tank and oriented with centerline perpendicular to the centerline of the transmitter coil 1312. The transmitter coil 1312 is excited at a certain constant frequency while the receiver coil 1322 monitors any received signals. The received signal is nulled or reduced to a minimum amount of electronic noise with respect to the tank condition, whether full or empty. As the fluid level changes near the fluid interface zone of influence, the amplitude and phase of the received signal changes. The point at which the received signal phase changes is the centerline of the receiver Rx 1322. By real time precise monitoring of the phase change, the point level determination is achieved. One application of a device in this configuration is a high level or low level sensor in storage tanks. Unlike a ferromagnetic tank application, the permeability of the non-ferromagnetic tank wall is already near unity by virtue of the non-ferromagnetic materials of construction.

Figure 13A:
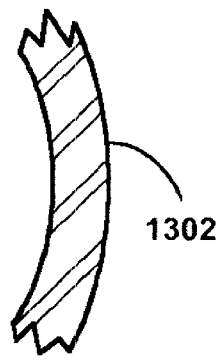
FIG. 13A is a cross-section of the ferromagnetic tank illustrated in FIG. 13 along the section line A—A showing no eddy currents within the walls of the non-ferromagnetic tank.

FIG. 13A is a cross-section of the ferromagnetic tank illustrated in FIG. 13 along the section line A—A showing no eddy currents within the walls of the non-ferromagnetic tank. FIG. 13A illustrates a cross-section of a ferromagnetic tank 102 wall across the tank from the embodiment of the sensor 1300. As shown in FIG. 13A, no significant eddy currents exist away from the embodiment.

Figure 14:
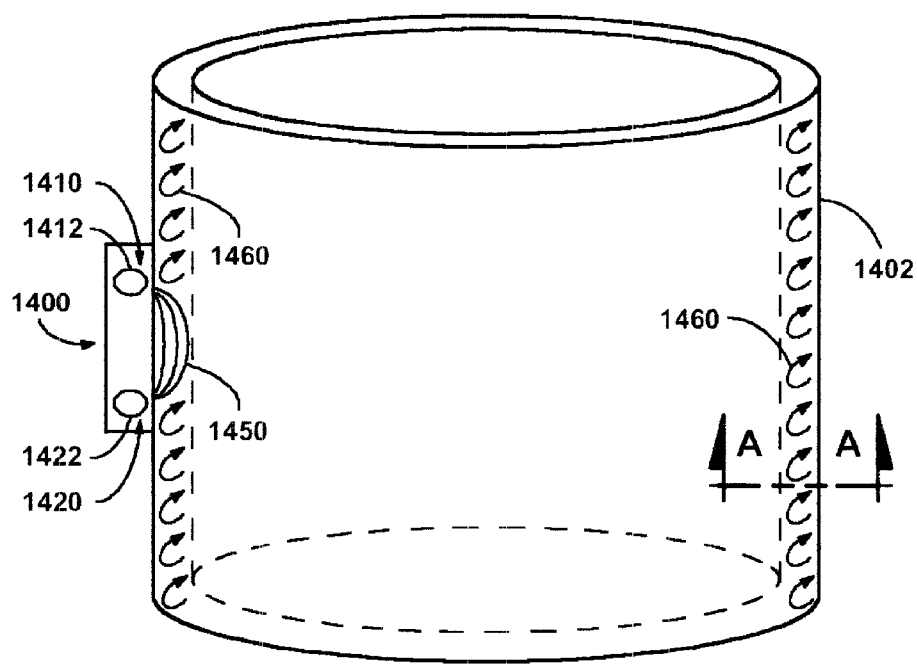
FIG. 14 illustrates an embodiment of a full range magnetic level gauge used to generate an accurate measurement over the full range of a non-ferromagnetic tank.

FIG. 14 illustrates an embodiment of a full range magnetic level gauge sensor 1400 used to generate an accurate measurement over the full range of a non-ferromagnetic tank. FIG. 14 illustrates an embodiment of a full range magnetic level gauge sensor 1400 used with in conjunction with a non-ferromagnetic tank 1402. A transmitter coil 1412 located near the non-ferromagnetic tank wall. A receiver coil 1422 located near the non-ferromagnetic tank 1402 and oriented with centerline perpendicular to the centerline of the transmitter coil 1412. The transmitter coil 1412 is excited at a certain constant frequency while the receiver coil 1422 monitors any received signals. By creating an efficient transmitter and receiver design in conjunction with the optimum choice of transmitter frequency, an apparatus capable of energizing the tank wall and monitoring changes of the received signal allows full range tank measurement of fluid level. The received signal is nulled or reduced to a minimum amount of electronic noise with respect to the tank condition, whether full or empty. As the fluid level changes in the tank, the fluid influences the amplitude and phase of the received signal. By real time precise monitoring of the signal, the full range level determination is achieved. One application of a device in this configuration is a full range fluid level sensor used in tanker cars for rapid discharge of fluid from the tank. The saturation coil setting determines the amount of transparency created through which the transmitted signal will penetrate. If the saturation current is too high, the signal penetrates the tank wall and eddy currents are not created within the wall. If the saturation current is too low, the signal will not penetrate the exterior of the tank wall which will also prevent eddy currents from developing within the tank wall.

Figure 14A:
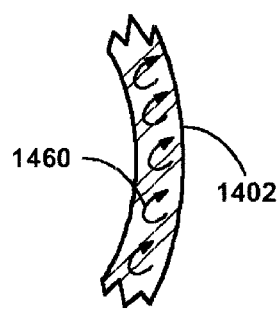
FIG. 14A is a cross-section of the ferromagnetic tank illustrated in FIG. 14 along the section line A—A showing eddy currents within the walls of a non-ferromagnetic tank.

FIG. 14A is a cross-section of the ferromagnetic tank illustrated in FIG. 14 along the section line A—A showing eddy currents within the walls of a non-ferromagnetic tank. FIG. 14A illustrates a cross-section of the non-ferromagnetic tank wall across the tank from the embodiment of the sensor 1400. As shown in FIG. 14A, significant eddy currents exist away from the sensor 1400. Thus, the tank walls act as an extension of the sensor 1400 of the apparatus to allow full range sensing of a non-ferromagnetic tank.

Figure 15:
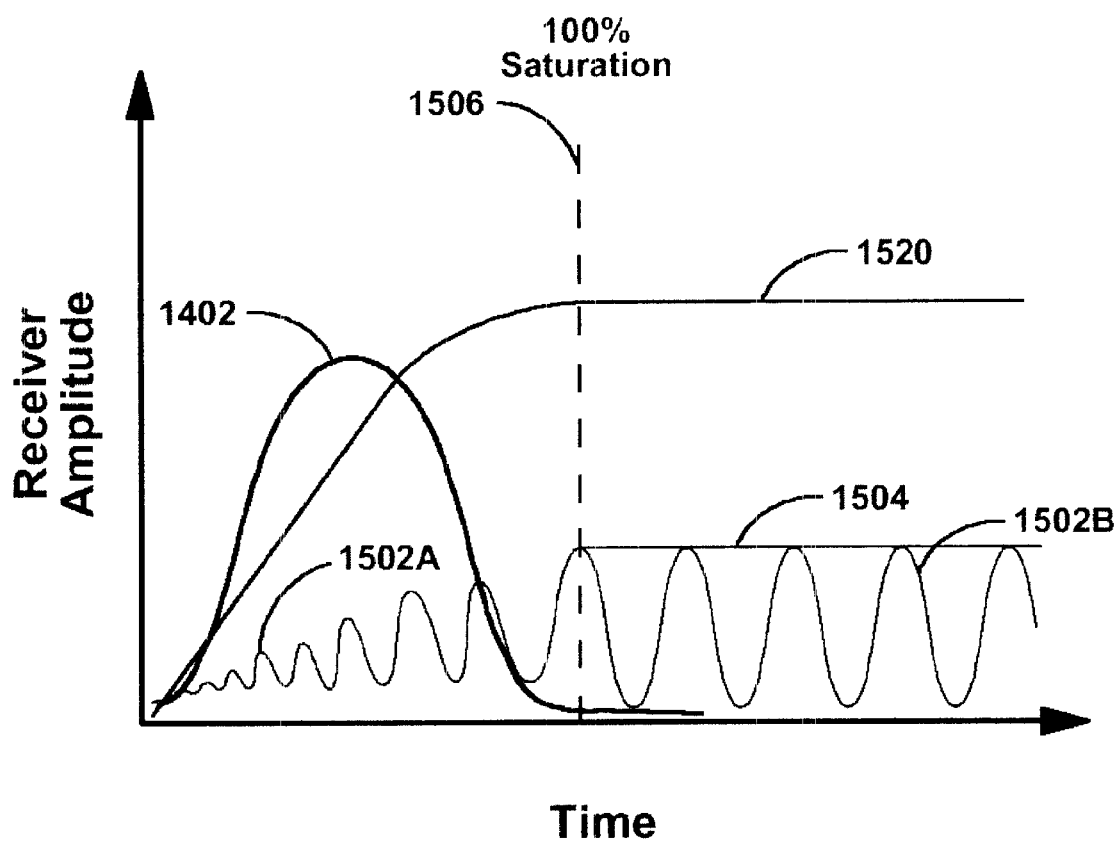
FIG. 15 illustrates the effect of saturation on the receiver amplitude compared to the transmitter strength in the wall.

FIG. 15 illustrates the effect of saturation on the receiver amplitude compared to the transmitter strength in the wall. The receiver amplitude 1502A starts with a small amplitude prior to saturation. At saturation, the receiver signal 1502B reaches its maximum 1504. The transmitter strength 1530 in the wall is illustrated as a comparison.

Figure 16:
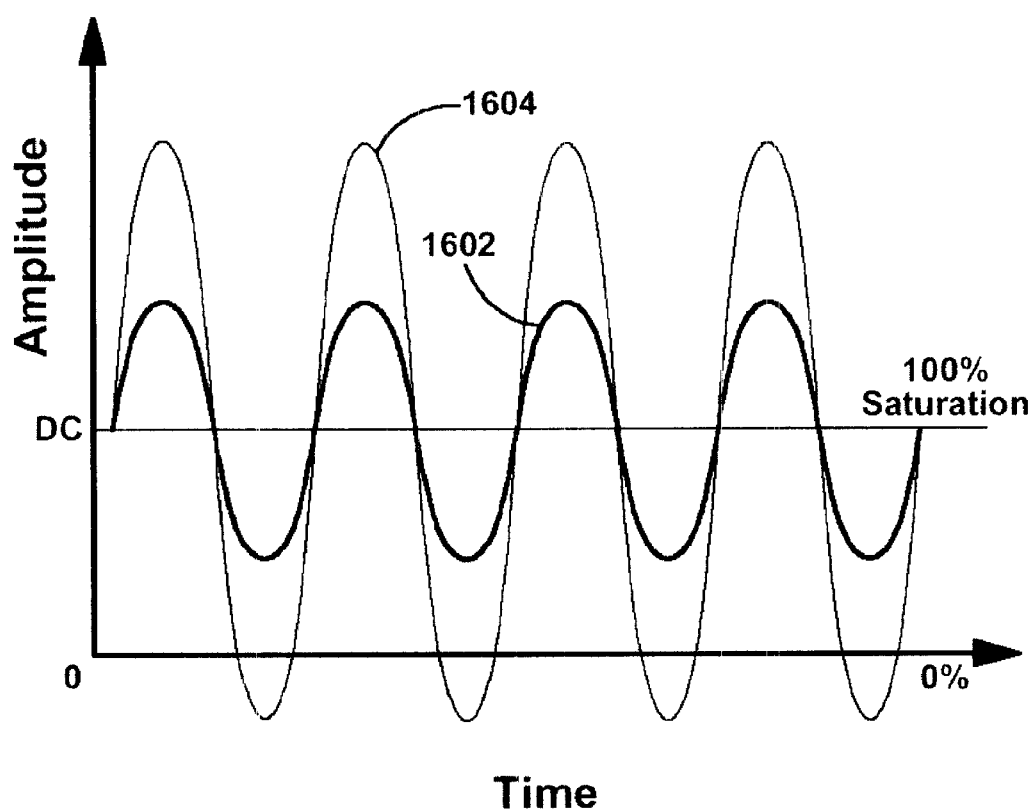
FIG. 16 is an amplitude versus time graph comparing the saturating DC current and the transmitting AC current.

FIG. 16 is an amplitude versus time graph comparing the saturating DC current 1602 and the transmitting AC current 1604. When the transmitting AC current 1604 swings to a negative value, it has the tendency to drive the signal out of saturation.

Figure 17:
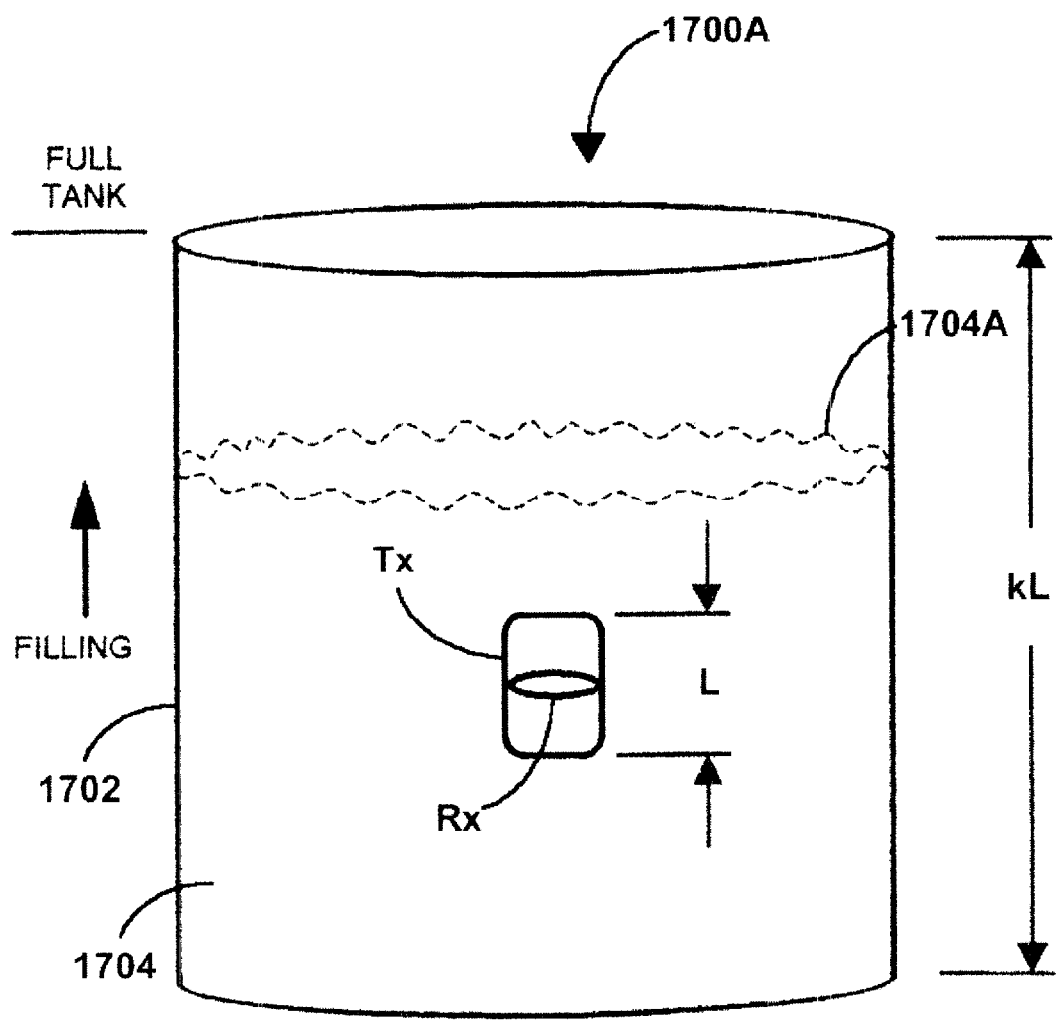
FIG. 17 is an illustration of an application of the present invention utilizing a loop transmitter with a tank for detecting the level within the tank.
Figure 18:
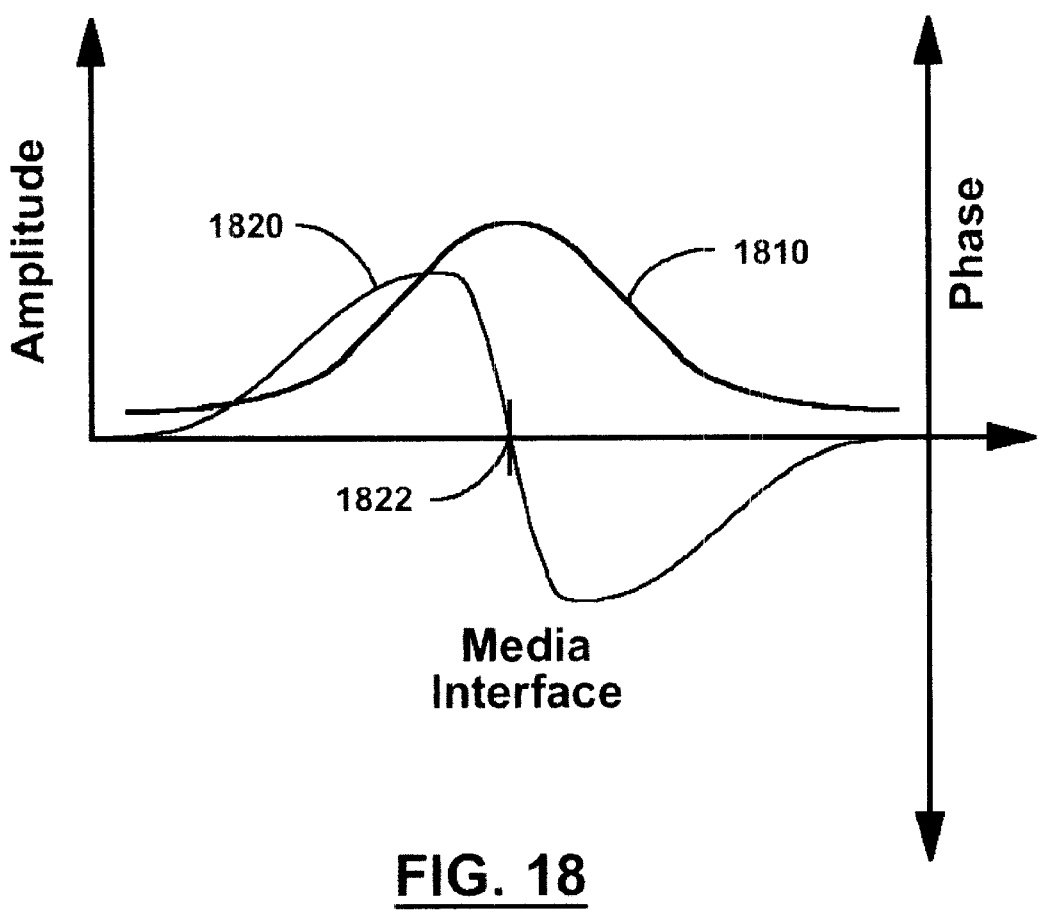
FIG. 18 is a graph of the output of the embedded transmitter/receiver configuration as illustrated in FIG. 17.

FIG. 17 is an illustration of an application of the present invention utilizing a loop transmitter with a tank for detecting the level within the tank. FIG. 17 is an illustration of an application of the present invention utilizing a loop transmitter Tx with a tank 1702 for detecting the level 1706A within the tank 1702 or the resistivity. The tank 1702 is illustrated having embedded transmitter/receiver configuration. The transmitter Tx has a diameter L. The receiver Rx can be moved within the transmitter Tx throughout the distance L. The tank 1702 is provided having a distance of k times that of the movable area for the receiver Rx within the transmitter Tx. Thus, the tank 1702 has depth of kL. The transmitter/receiver configuration can be nulled with water in the tank. As the water starts to fill the tank as the target material, the null signal is offset until such time as the water engages the location of the receiver Rx which would be the maximum offset of the null. As the fluid continues to fill the tank, the null signal would decrease to a lower value. FIG. 18 is a graph of the output of the embedded transmitter/receiver configuration as illustrated in FIG. 17. As the fluid begins entering the tank, the volts detected increases 1810. The volts detected will continue to increase until such point as the fluid is located congruent with the receiver Rx, which will be the maximum amplitude 1810. As the fluid continues to fill the tank, nulling offset will decrease and approach the nulled value 1810. The phase of the signal 1820 is disposed over the amplitude 1810 such that the phase increases to a maximum point and as the fluid engages the receiver Rx, the phase 1820 decreases and passes through the zero axis as the fluid rises above the receiver Rx. The phase has a corresponding configuration in the negative as it had in the positive of the graph.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. The method for detecting a liquid level inside a ferromagnetic tank and resistivity within a tank to determine material characteristics associated with the tank comprising the steps (a) testing empirically to approximate the conductivity of the ferromagnetic tank wall;

(b) testing empirically to approximate the permeability of the ferromagnetic tank wall;

(c) creating a first set of electromagnetic waves adjacent to and electrically isolated from the outside tank wall to be measured of a relatively low frequency;

(d) impinging the first set of electromagnetic waves on the tank wall for saturating the tank wall;

(e) creating a second set of electromagnetic waves having specific constant amplitude of a higher frequency than the first set of electromagnetic waves, the second set of electromagnetic waves for engaging the tank wall also adjacent to and electrically isolated from the outside tank wall and generating a sensing signal having modified characteristics; and (f) receiving the sensing signal through the saturated tank wall such that the modified characteristics of the sensing signal are processed to determine the required information of liquid level and/or liquid type.

2. The method of claim 1 wherein the empirical testing of the ferromagnetic tank wall conductivity and permeability comprises the steps of:

(a) generating and transmitting a plurality of electromagnetic waves adjacent to and electrically isolated from a tank wall;

(b) impinging the tank wall with at least one first electromagnetic wave of relatively low frequency having a constant amplitude;

(c) impinging the tank wall with at least one second electromagnetic wave of constant amplitude and adjustable higher frequency than the first electromagnetic wave and generating a sensing signal;

(d) increasing the frequency of the second wave and monitoring the sensing signal;

(e) measuring the frequency of the second wave when the sensing signal does not change with an increase in frequency and does change with a decrease in the frequency of the second wave;

(f) impinging the tank wall with one or more third constant low frequency electromagnetic wave of known and variable current;

(g) impinging the tank wall with a fourth electromagnetic wave of constant frequency and amplitude and monitoring the sensing signal generated by the fourth wave;

(h) varying the current of the third wave;

(i) measuring the current of the third wave when the sensing signal does not change with increases in the current of the third wave and changes with a decrease in the current; and (j) using the measured values of amplitude, current, and frequency of the electromagnetic waves to calculate the permeability and conductivity of the tank wall.

3. The method of claim 1 further comprising:

(a) impinging the ferromagnetic tank wall with the first set of relatively low frequency electromagnetic waves sufficient to reduce the permeability of a portion of the tank wall;

(b) impinging the ferromagnetic tank wall with the second set of electromagnetic waves to induce eddy currents within the tank wall; and (c) using the eddy currents to generate a sensing signal within the contents of the tank that is available for reception.

4. The invention of claim 1, 2 or 3 further comprising creating a nulled relationship between the at least one electromagnetic wave transmitter and a sensing signal receiver.

5. A method for detecting the presence of liquid at a determined level within a ferromagnetic tank comprising:

(a) creating a first set of electromagnetic waves of a relatively low frequency adjacent to and electrically isolated from an outer surface of a tank wall;

(b) impinging the first electromagnetic waves on the tank wall for saturating a portion of the tank wall from the outer surface through the inside wall surface;

(c) creating and transmitting adjacent to and electrically isolated from the outside tank wall a second set of electromagnetic waves of a higher frequency than The first set of electromagnetic waves through the saturated portion of the tank wall available for generating a sensing signal within the liquid adjacent to the inner surface of the saturated portion of the tank wall; and (d) placing a receiver adjacent to and electrically isolated from the outer surface of the tank wall for receiving the sensing signal.

6. The method of claim 5 wherein the receiver has a nulled relationship to at least one of the first or second sets of electromagnetic waves.

7. An apparatus for detecting a level or resistivity of a liquid inside a ferromagnetic tank comprising:

(a) an electromagnetic wave transmitter adjacent to and electrically isolated from the outside tank wall capable of generating a first set of relatively low frequency electromagnetic waves that can at least partially saturate a portion of the tank wall;

(b) an electromagnetic wave transmitter adjacent to and electrically isolated from the outside tank wall capable of generating a second higher frequency set of electromagnetic waves;

(c) an electromagnetic wave receiver having a nulled relationship to the transmitter for receiving a sensing signal induced from a liquid inside the tank and resulting from the action of the higher frequency electromagnetic waves.

8. The apparatus of claim 7 wherein the frequency and amplitude of the first and second sets of electromagnetic waves can be controllably varied.

9. The apparatus of claim 7 wherein the liquid level or resistiviy is measured when adjacent to one or more single points at the inside tank wall surface.

10. The apparatus of claim 7 wherein the transmitter of the first set and of the second set of electromagnetic waves has the small axis of orientation.

\* \* \* \* \*